United States Patent
Gilson et al.

(10) Patent No.: US 8,383,382 B2
(45) Date of Patent: Feb. 26, 2013

(54) VARIANT LOVD POLYPEPTIDES AND THEIR USES

(75) Inventors: Lynne Gilson, Redwood City, CA (US); Steven James Collier, The Galen (SG); Joly Sukumaran, The Galen (SG); Wan Lin Yeo, The Galen (SG); Oscar Alvizo, Redwood City, CA (US); Ee Ling Teo, The Galen (SG); Robert John Wilson, The Galen (SG); Junye Xu, The Galen (SG)

(73) Assignee: Codexis, Inc., Redwood City, CA (US)

( * ) Notice: Subject to any disclaimer, the term of this patent is extended or adjusted under 35 U.S.C. 154(b) by 91 days.

(21) Appl. No.: 12/890,134

(22) Filed: Sep. 24, 2010

(65) Prior Publication Data

US 2011/0111468 A1    May 12, 2011

Related U.S. Application Data

(60) Provisional application No. 61/247,253, filed on Sep. 30, 2009, provisional application No. 61/247,274, filed on Sep. 30, 2009.

(51) Int. Cl.
*C12N 9/10*   (2006.01)
*C12Q 1/48*   (2006.01)
*C12P 17/06*  (2006.01)
*C07H 21/06*  (2006.01)

(52) U.S. Cl. .......... 435/193; 435/15; 435/125; 536/23.2
(58) Field of Classification Search .................. None
See application file for complete search history.

(56) References Cited

U.S. PATENT DOCUMENTS
2009/0191602 A1    7/2009   Tang et al.

FOREIGN PATENT DOCUMENTS
WO    WO 93/23547    * 11/1993

OTHER PUBLICATIONS

UniProt Accession No. B0Y1H9, created Apr. 8, 2008.*
PCT International Search Report and Written Opinion from PCT/US10/50249 dated Feb. 14, 2011.
Gao et al., 2009, "Directed Evolution and Structural Characterization of a Simvastatin Synthase," *Chemistry and Biology* 16:1064-1074.
Xie et al., 2009, "Rational Improvement of Simvastatin Synthase Solubility in *Escherichia Coli* Leads to Higher Whole-Cell Biocatalytic Activity," *Biotechnology and Bioengineering* 102(1):20-28.

* cited by examiner

*Primary Examiner* — Anand Desai
*Assistant Examiner* — Iqbal H Chowdhury
(74) *Attorney, Agent, or Firm* — Codexis, Inc.

(57) ABSTRACT

The present disclosure provides acyltransferases useful for synthesizing therapeutically important statin compound.

17 Claims, 3 Drawing Sheets

Figure 1:
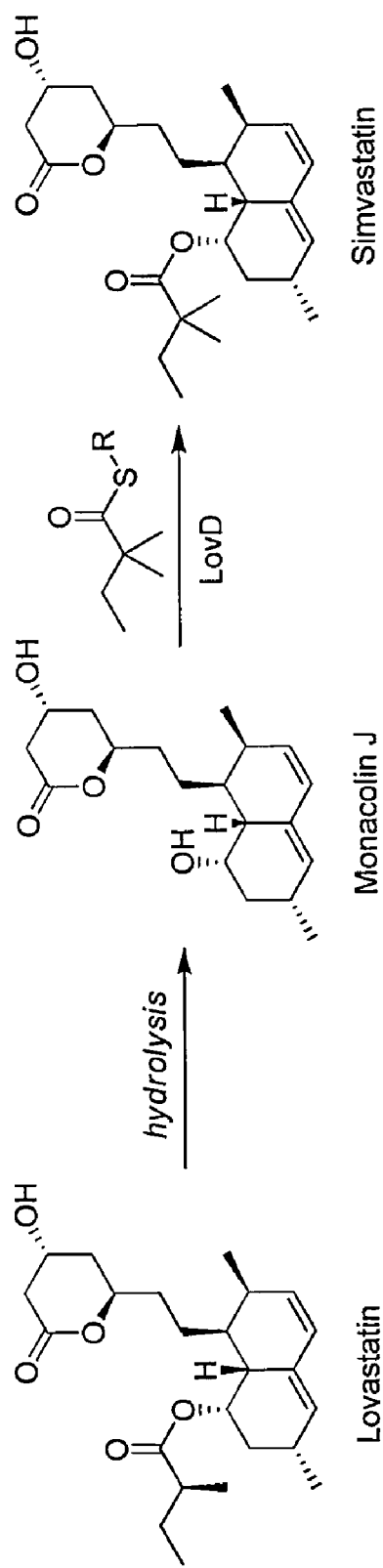

**Codon optimized *Aspergillus terreus* Polynucleotide – SEQ ID NO: 1**

ATGGGTTCTATCATTGATGCGGGCTGCGGCCCGGACCCGGTGGTTCGATGAAACGGCTTTCCGTAAAGCGGTTAAAA
GCCGCCAGATTCCGGGTGCTGTTATTATGGCGGTGATTGTAGTGGTAACCTGAACTACACTCGCTGTTCGGCACG
CACTGTGCTGCGACGAGTGCAATTACCACCGCTGCAGGTGGATACACCATGTCGTCTGGCAAGCGCTACTAA
ATTACTGACCAGATTATGGCACTGCAGTGCATGGAACGCGGCCTGGTAGACTTGGATGAAACTGTTGACCGCCTGCTG
CCGGACCTGAGCGCGATGCCGGTGCTGGAAGGCTTTGATGATGCCGGCAACGCCCGTCGCCGCGAACGCCGTGGTAAA
ATTACGTTACGCCATCTGCTGACACACACCAGGTCGTCTCCTGCTACGTCTCGTACGTCTCCTGCATCCGCTGCTGCGGGAGTATATGG
CCCAGGGTCATTTGCAGAGCGCTGAGAAGTTTGGCATTCAGTCTCGTCGTCGGCCGCCAGCTGTAATGATCCAGGCGC
GGAATGGATTATGCGCTAATCTGAAACTGGACTGGGCCGCTGGGCATCACTGATATGACGTTCAAACTGCCGGATATGCTGGCA
CTTGCAGGAGAACATTGCGCGCCACCGCAACTCCCGGATGGTCTCGCTATGATGACTCTGTGTATTTCGCGGACG
CGTCGTGCCAGCAGACCGCAGGGCCAGGCGTGTTCAGCGGCCAGGCAGTTACATGAAGGTTCGACTCTCTGCTGAAACG
GTGAAGAGTGTTCGGGGGCCAGGCACAAACCGTGATCTGATGTTCCAGCGGGCCTGGAACCGGCTTGAAGAACAAAT
TGACGGCCTGTGCTGCAGCCACATATGACGCGTCCCGCACAATCAACTATGGCGTCCAATGCTGTCCTGCGTCGGCCTG
GAACCAGCATATGACGCGTCCCGCACAAACCGTGATCTGATGTTCCAGCGGGCCTGGAACCGGCTTGAAGAACAAAT
GGTGGTATCATTGCACTGGAGGATCTGATGGTGAGAACTGGCGTCGTAAAGGCTCGCTGACGTTTGGGGGTCCA
AACATTGTTGGCAGATTGACCGGAAAGCGGGTCTGTGTACTTTAGCCTTTTCCAGCTGGAACGTGGAACGACCCGG
TGTGTCGTGACCTGACTCGCACCTTTGAGCACGGATCTATGCACAGTATCAACAGGGCTAA

*FIGURE 2*

*Aspergillus terreus* Polypeptide – SEQ ID NO: 2

MGSIIDAAAAADPVVLMETAFRKAVKSRQIPGAVIMARDCSGNLNYTRCFGARTVRRDEC

NQLPPLQVDTPCRLASATKLLTTIMALQCMERGLVDLDETVDRLLPDLSAMPVLEGFDDA

GNARLRERRGKITLRHLLTHTSGLSYVFLHPLLREYMAQGHLQSAEKFGIQSRLAPPAVN

DPGAEWIYGANLDWAGKLVERATGLDLEQYLQENICAPLGITDMTFKLQQRPDMLARRAD

QTHRNSADGRLRYDDSVYFRADGEECFGGQGVFSGPGSYMKVLHSLLKRDGLLLQPQTVD

LMFQPALEPRLEEQMNQHMDASPHINYGGPMPMVLRRSFGLGGIIALEDLDGENWRRKGS

LTFGGGPNIVWQIDPKAGLCTLAFFQLEPWNDPVCRDLTRTFEHAIYAQYQQG

*FIGURE 3*

VARIANT LOVD POLYPEPTIDES AND THEIR USES

1. CROSS REFERENCE TO RELATED APPLICATIONS

This application claims the benefit under 35 U.S.C. §119 (e) of U.S. provisional application Nos. 61/247,253 and 61/247,274, both filed Sep. 30, 2009, the contents of all of which are incorporated herein in their entireties by reference thereto.

The Sequence Listing concurrently submitted herewith under 37 CFR §1.821 in a computer readable form (CRF) via EFS-Web as file name CX2-022.txt is incorporated herein by reference. The electronic copy of the Sequence Listing was created on Sep. 24, 2010, with a file size of 52 Kbytes.

2. BACKGROUND

Simvastatin is a semi-synthetic analog of the natural fungal polyketide lovastatin which can be isolated from the fermentation broth of *Aspergillus terreus*. Simvastatin and lovastatin are both marketed by Merck Co. as cholesterol-lowering drugs that reduce the risk of heart disease: simvastatin as ZOCOR® and lovastatin as MEVACOR®.

Lovastatin (illustrated in FIG. 1) is a potent inhibitor of hydroxymethylglutaryl coenzyme A reductase, the rate-limiting enzyme in the cholesterol biosynthetic pathway (Xie et al., 2006, Chemistry & Biology 13:1161-1169). The analog simvastatin (also illustrated in FIG. 1) is more effective in treating hypercholesterolemia (Manzoni & Rollini, 2002, Appl. Microbiol. Biotechnol. 58:555-564; Istan & Diesenhofer, 2001, Science 292:1160-1164). Substitution of the α-methylbutyrate side chain of lovastatin with the α-dimethylbutyrate side chain found in simvastatin significantly increases its inhibitory properties while lowering undesirable side effects (Klotz, Ulrich, 2003, Arzneimittel-Forschung 53: 605-611).

Because of the clinical importance of simvastatin, various multi-step syntheses starting from lovastatin have been described (see, e.g., WO 2005/066150; US Application No. 2005/0080275; US Application No. 2004/0068123; U.S. Pat. No. 6,833,461; WO 2005/040107; Hoffman et al., 1986, J. Med. Chem. 29:849-852; Schimmel et al., 1997, Appl. Environ. Microbiol. 63:1307-1311).

The gene cluster for lovastatin biosynthesis has been previously described (see, e.g., U.S. Pat. No. 6,391,583; Kennedy et al., 1999, Science 284:1368-1372; Hutchinson et al., 2000, Antonie Van Leeuwenhoek 78:287-295). Encoded in this gene cluster is the 46 kD enzyme LovD, which catalyzes the last step of lovastatin biosynthesis.

Briefly, the decalin core and HMG-CoA moieties that mimic portions of the lovastatin compound are synthesized in vivo by lovastatin nonaketide synthase (LNKS) and three accessory enzymes. The 2-methylbutyrate side chain of lovastatin is synthesized in vivo by lovastatin diketide synthase (LDKS) and covalently attached to the acyl carrier domain of LovF via a thioester linkage. LovD, an acyltransferase, is then able to selectively transfer the 2-methylbutyrate group from LDKS to the C8 hydroxyl group of monacolin J in a single step to yield lovastatin (Xie et al., 2006, Chemistry & Biology 13:1161-1169).

It has recently been discovered that the LovD acyltransferase has broad substrate specificity towards the acyl carrier, the acyl substrate and the decalin acyl acceptor (Xie et al., 2006, Chem. Biol. 13:1161-1169). For example, LovD can efficiently catalyze acyl transfer from CoA thioesters or N-acetylcysteamine ("SNAC") thioesters to monacolin J (id.). Significantly, when α-dimethylbutyryl-SNAC was used as the acyl donor, LovD was able to convert monacolin J and 6-hydroxy-6-desmethyl monacolin J into simvastatin and huvastatin, respectively (id.). Using an *E. coli* strain engineered to overexpress LovD as a whole-cell biocatalyst, preparative quantities of simvastatin were synthesized in a single fermentation step (id.).

The above studies demonstrate that LovD acyltransferase is an attractive enzyme for the biosynthesis of pharmaceutically important cholesterol-lowering drugs such as simvastatin. However, in subsequent experiments carried out with isolated LovD enzyme, stability and reaction rate proved problematic (Xie & Tang, 2007 Appl. Environ. Microbiol. 73:2054-2060). Specifically, it was found that LovD precipitates readily (hours) at high protein concentrations (~100 μM) and slowly (days) at lower concentrations (~10 μM) (id.). In addition, it was found that the very desired product, simvastatin, competes for the LovD enzyme, significantly impeding the overall net rate of acylation (id.).

The LovD enzyme is also highly prone to mis-folding and aggregates when over-expressed in *E. coli*, making even whole-cell biocatalysis systems less than ideal for commercial production (Xie et al., 2009, Biotech. Bio Eng. 102:20-28).

In an effort to increase LovD solubility without loss of catalytic activity, mutants of wild-type *A. terreus* LovD have been studied. Replacing the cysteine residues at positions 40 and 60 (Cys40 and Cys60) with alanine residues yielded improvements in both enzyme solubility and whole-cell biocatalytic activity (id.). Further mutagenesis experiments converting these two residues to small or polar amino acids showed that Cys40→Ala ("C40A") and Cys60→Asn ("C60N") mutations are the most beneficial, yielding 27% and 26% increases, respectively, in whole-cell biocatalytic activity (id.). When combined, these mutations proved additive, with the C40A/C60N double mutant exhibiting approximately 50% increases in both solubility and whole-cell biocatalytic activity.

Despite their improved properties, these LovD mutants are unsuitable for large scale production of simvastatin in cell-free systems. Additional variants or mutants of wild-type *A. terreus* LovD enzymes that exhibit improved properties as compared to the wild-type and/or known mutants would be desirable.

3. SUMMARY

As discussed above, the LovD gene of *A. terreus* encodes an acyl transferase (hereinafter called "LovD polypeptide," "LovD enzyme," "LovD acyltransferase" or "LovD") capable of converting monacolin J, the hydrolysis product of the natural product lovastatin, to simvastatin. The inventors of the present disclosure have discovered that LovD polypeptides including mutations at certain residue positions exhibit improved properties as compared to the wild-type LovD polypeptide produced by *A. terreus* (SEQ ID NO:2).

Accordingly, in one aspect, the present disclosure provides variant LovD polypeptides that have one or more improved properties as compared to wild-type LovD polypeptide from *A. terreus* (SEQ ID NO:2). Generally, the LovD variants include one or more mutations at selected positions that correlate with one or more improved properties, such as increased catalytic activity, increased thermal stability, reduced aggregation and/or increased stability to cell lysis conditions. The variant LovD polypeptides can include one or more mutations from a single category (for example, one or more mutations that increase catalytic activity), or mutations from two or more different categories. By selecting mutations correlating with specific properties, variant LovD polypeptides suitable for use under specified conditions can be readily obtained.

Positions in the wild-type LovD polypeptide sequence of SEQ ID NO:2 at which mutations have been found that correlate with one or more improved properties, such as increased catalytic activity include, but are not limited to, A123, M157, 5164, S172, L174, A178, N191, L192, A247, 8250, 5256, A261, G275, Q297, L361, V370 and N391. Additional positions at which mutations have been found which correlate with one or more improved properties, such as thermal stability, include, but are not limited to, Q241, A261, Q295 and Q412. Yet further positions at which mutations have been found that correlate with one or more improved properties, such as reduced aggregation, include but are not limited to, N43, D96 and H404. Positions at which mutations were found that correlated with one or more improved properties, such as increased stability included, but are not limited to, C40, C60 and D254.

Positions in the wild-type LovD polypeptide sequence of SEQ ID NO:2 at which mutations having no detrimental effect (or at which mutations improved the properties of the LovD enzyme) were found include, but are not limited to, I4, A9, K26, R28, I35, C40, S41, N43, C60, S109, S142, A184V, N191S, A261, L292, Q297, L335, A377, A383, N391 and H404. Particular embodiments with improved properties can include, but are not limited to, LovD polypeptides with mutations at positions L174 and A178, and optionally from zero to about 30 additional mutations. In a specific embodiment, the additional mutations are at positions selected from the positions identified above. In some embodiments, LovD polypeptides with improved properties include mutations at positions A123, L174, A178, N191, A247 and L361, and from zero up to about 26 additional mutations. In a specific embodiment, the additional mutations are at positions selected from the positions identified above.

Specific, exemplary mutations of the wild-type LovD polypeptide of SEQ ID NO:2 that correlate with increased catalytic activity include, but are not limited to, A123P, M157V, S164G, S172N, L174F, A178L, N191G, L192I, A247S, R250K, S256T, A261H, G275S, Q297G, L361M, V370I and N391S.

Specific, exemplary mutations of the wild-type LovD polypeptide of SEQ ID NO:2 that correlate with increased thermal stability include, but are not limited to, Q241M, A261H, Q295R and Q412R.

Specific, exemplary mutations of the wild-type LovD polypeptide of SEQ ID NO:2 that correlate with reduced aggregation include, but are not limited to, N43R, D96R and H404K.

Specific exemplary mutations of the wild-type LovD polypeptide of SEQ ID NO:2 that correlate with increased stability include, but are not limited to, C40R, C60R and D254E.

In addition to the specific, exemplary mutations disclosed above, it has been discovered that LovD polypeptides can tolerate a range of additional specific mutations at other positions without detrimental effect. Indeed, in some instances, the additional mutations also confer the LovD polypeptides with beneficial or improved properties. These additional mutations include, but are not limited to, the following specific and exemplary mutations: I4N, A9V, K26E, R28K, R28S, I35L, C40A, C40V, C40F, S41R, N43Y, C60F, C60Y, C60N, C60H, S109C, S142N, A184T, A184V, N191S, A261T, A261E, A261V, L292R, Q297E, L335M, A377V, A383V, N391D and H404R. Variant LovD polypeptides may include one or more mutations at these additional positions.

In some embodiments, the variant LovD polypeptides described herein include the following two mutations: L174F and A178L, and optionally from zero to about 30 additional mutations. In a specific embodiment, the optional additional mutations are selected from the various mutations identified above.

In some embodiments, the variant LovD polypeptides described herein will include at least the following mutations: A123P, L174F, A178L, N191(S or G), A247S and L361M, and from zero up to about 26 additional mutations selected from the various different mutations identified above.

In general, variant LovD polypeptides including greater numbers of mutations exhibit greater catalytic activity. For example, whereas a specific variant including mutations at two residue positions (L174F and A178L) exhibited approximately two-fold greater activity than wild-type LovD activity, and a specific variant including mutations at six residue positions (Variant 120 in Table 1) exhibited approximately 12-fold greater catalytic activity than wild-type LovD, one specific variant including 28 mutations (Variant 114 in Table 1), one specific variant including 29 mutations (Variant 116 in Table 1) and one specific variant including 32 mutations (Variant 118 in Table 1) each exhibited approximately 1550-fold greater catalytic activity than wild-type LovD. Table 1 discloses numerous variant LovD polypeptides exhibiting from about 10- to about 1550-fold greater activity than the wild-type LovD polypeptide of SEQ ID NO:2. Using these exemplary specific variant LovD polypeptides, additional LovD variant polypeptides having greater than about 10-, 20-, 30-, 40-, 50-, 60-, 70-, 80-, 90-, 100-, 150-, 200-, 300-, 400-, 500-, 600-, 700-, 800-, 900-, 1000-, 1100-, 1200-, 1300-, 1400-, 1500-, 1600-, 1700-fold, or even greater, activity than the wild-type LovD polypeptide of SEQ ID NO:2 can be readily obtained.

The specific variant LovD polypeptides of Table 1 can also be used to readily obtain variant LovD polypeptides that have specified combinations of improved properties.

The various variant LovD polypeptides described herein may also optionally include one or more conservative mutations in addition to the mutations described above. Typically, such optional conservative mutations will not comprise more than about 20%, 15%, 10%, 8%, 5%, 3%, 2%, or 1% of the overall sequence. Without intending to be bound by any particular theory of operation, it is believed that the amino acid at position 76 may be involved in catalysis. Mutations at this residue position should be preferably avoided. It is also believed that the amino acids at position 79, 148, 188 and/or 363 may contribute to catalysis. In some embodiments, variant LovD polypeptides that include optional conservative mutations will contain from 1 to 20 such mutations. In additional embodiments, variant LovD polypeptides include truncated polypeptides wherein 1 to 15 amino acids may be omitted from the N-terminus and 1 to 6 amino acids may be omitted from the C-terminus.

In another aspect, the disclosure provides polynucleotides encoding the variant LovD polypeptides described herein. In some embodiments the encoding polynucleotides are part of an expression vector comprising one or more control sequences suitable for directing expression of the encoding sequence in a host cell. In some embodiments, the expression vector is suitable for expressing variant LovD polypeptides in a bacterium, such as but not limited, to an *E. coli*, and includes a promoter sequence, such as a lac promoter sequence, operably linked to the encoding sequence. In such polynucleotides the codons of the encoding sequence can be optimized for expression in a particular host cell of interest.

In yet another aspect, the present disclosure provides host cells comprising a variant LovD encoding polynucleotide or expression vector. In some embodiments, the host cell is a bacterium such as but not limited to *E. coli*. The host cells can be used to produce crude or purified preparations of specific variant LovD polypeptides, or, alternatively, they can be used as whole-cell preparations in the methods described herein to produce simvastatin and huvastatin.

The variant LovD polypeptides described herein esterify the C8 hydroxyl group of monacolin J in the presence of an α-dimethylbutyryl thioester co-substrate to yield simvastatin. Accordingly, in another aspect, the present disclosure provides methods of making simvastatin utilizing the variant LovD polypeptides described herein. The methods generally comprise contacting monacolin J with a variant LovD polypeptide in the presence of an α-dimethylbutyryl thioester co-substrate under conditions which yield simvastatin. In some embodiments, analogues of monacolin J may be used as precursor substrates to the formation of other statins, such as, but not limited to, huvastatin.

The variant LovD polypeptides described herein recognize a number of different α-dimethylbutyryl thioester co-substrates, including by way of example and not limitation, α-dimethylbutyryl-S—N-acetylcysteamine ("DMB-S-NAC"), α-dimethylbutyryl-S-methylthioglycolate ("DMB-S-MTG"), α-dimethylbutyryl-S-methyl mercaptopropionate "DMB-S-MMP"), α-dimethylbutyryl-S-ethyl mercaptoproprionate ("DMB-S-EMP"), α-dimethylbutyryl-S-methyl mercaptobutyrate ("DMB-S-MMB"), and α-dimethylbutyryl-S-merceaptopropionic acid ("DMB-S-MPA"). Any of these thioester co-substrates, or mixtures of such thioester co-substrates, can be used in the methods described herein.

In some embodiments, the reaction is carried out in vitro with an isolated variant LovD polypeptide, which can be purified or unpurified prior to use. In some embodiments, enzyme tags may be added to either terminus of the LovD polypeptide in order to enable binding to a solid carrier. In some specific embodiments, the variant LovD polypeptide is isolated and purified prior to use. In other specific embodiments, the variant LovD polypeptide is supplied as a crude lysate of host cells engineered to express the variant LovD polypeptide, with or without removal of the cell debris from the cell lysate.

The monacolin J substrate can be included in the reaction mixture in purified form, or, alternatively, it can be generated in situ by hydrolysis of lovastatin. Accordingly, in some embodiments, the reaction is carried out in a single pot as a two-step process starting from lovastatin.

The methods can be carried out under a variety of conditions, depending upon, among other factors, the activity of the specific variant LovD polypeptide being used. A typical reaction includes about 1 to 250 g/L, also 25 to 200 g/L, and often 1 to 200 g/L, monacolin J substrate or analogue thereof, excess thioester co-substrate (for example, from about 1.0 to 10.0 equiv, also 1.0 to 5.0 equiv, and often 1.0 to 4.0 equiv) and about 0.1 to 10 g/L LovD variant polypeptide. In some embodiments, a typical reaction may include 20 to 200 g/L, 50 to 200 g/L, or 50 to 150 g/L monacolin J substrate or analogue thereof. In some embodiments, a typical reaction may include from 1.0 to 2.0, from 1.0 to 1.5, or from 1.1 to 1.3 equivalents of thioester co-substrate. In some embodiments, 0.2 to 10 g/L, 0.5 to 10 g/L, 0.5 to 5 g/L, 0.75 to 2.5 g/L, or 0.75 to 1.5 g/L of LovD variant polypeptide may be used. The pH of the reaction mixture, the temperature at which the reaction is carried out and the duration of the reaction will depend upon, among other factors, the specific LovD variant polypeptide being used. Most reactions can be carried out at a pH in the range of pH 7.5 to pH 10.5, also pH 8.0 to pH 10.0, and often pH 8 to pH 9.5, and a temperature in the range of about 20 to 50° C., also 20 to 30° C., and often 20 to 40° C., for approximately 2 to 54 hrs, 5 to 48 hrs or 10 to 48 hrs. Reactions carried out with variant LovD polypeptides including mutations that correlate with increased thermal stability can be carried out at higher temperatures, typically in a range of about 30 to 40° C., depending upon the particular variant being used.

The thiol by-product of the acyl transfer reaction may inhibit LovD polypeptides. Accordingly, it may be desirable to include in the reaction mixture one or more scavenging agents that might improve reaction rate and/or yield by removing or scavenging these thiol by-products. Scavenging includes, without limitation, chemical modification of thiol by-products, such as by oxidation. Suitable scavenging agents may include, but are not limited to, compounds that react with the thiol by-product and agents capable of chelating, adsorbing, absorbing or removing the thiol by-product. In some embodiments where a scavenging agent is used, the scavenging agent is activated charcoal. When used, the activated charcoal can be included in the reaction mixture in quantities ranging from 1 to 30 g/L, 2 to 20 g/L and 5 to 15 g/L.

The monacolin J substrate may be in the form of a salt, such as an ammonium or sodium salt. Reaction of the monacolin J substrate, such as the sodium or ammonium salts of monacolin J, may optionally be run in the presence of a scavenger, such as activated charcoal. Monacolin J may also be in the form of an ammonium salt. When the ammonium salt of monacolin J is converted to the ammonium salt of simvastatin, the ammonium salt of simvastatin may be precipitated from the reaction medium, for example, from water.

Other aspects and advantages of the disclosure will be apparent from the detailed description that follows.

4. BRIEF DESCRIPTION OF THE FIGURES

FIG. 1 provides a diagram illustrating a pathway for synthesizing simvastatin from lovastatin or monacolin J;

FIG. 2 provides a polynucleotide sequence encoding wild type LovD enzyme from *Aspergillus terreus* that has been codon-optimized for expression in *E. coli*. (SEQ ID NO:1); and FIG. 3 provides the polypeptide sequence encoded by the sequence of FIG. 2 (SEQ ID NO:2).

5. DETAILED DESCRIPTION

In certain aspects, the present disclosure provides LovD variant polypeptides that are capable of transferring an acyl group from certain thioester co-substrates to monacolin J and analogs or derivatives thereof to yield therapeutically important statin compounds, such as but not limited to simvastatin and huvastatin. The LovD variants have improved properties as compared to the wild-type LovD acyltransferase obtainable from *A. terreus* (SEQ ID NO:2), and can be used in cell-based or cell-free systems to efficiently and cost-effectively produce statins such as simvastatin from readily available starting materials, such as lovastatin and monacolin J.

5.1. ABBREVIATIONS

For the purposes of the descriptions herein, the abbreviations used for the genetically encoded amino acids are conventional and are as follows:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When peptide or polypeptide sequences are presented as a string of one-letter or three-letter abbreviations (or mixtures thereof), the sequences are presented in the N→C direction in accordance with common convention.

5.2. DEFINITIONS

The technical and scientific terms used in the descriptions herein will have the meanings commonly understood by one of ordinary skill in the art, unless specifically defined otherwise. Accordingly, the following terms are intended to have the following meanings.

"Wild-type LovD," "Wild-type LovD enzyme," "Wild-type LovD polypeptide," and/or "Wild-type LovD acyltransferase" refers to the acyltransferase enzyme obtainable from *A. terreus* encoded by the LovD gene and having an amino acid sequence corresponding to SEQ ID NO:2. This enzyme can use a thioester to regiospecifically acylate the C8 hydroxyl group of monacolin J or 6-hydroxy-6-des-methyl monacolin J so as to produce simvastatin or huvastatin. See, e.g., Xie et al., 2006, "Biosynthesis of Lovastatin Analogs with a Broadly Specific Acyltransferase," Chem. Biol. 13:1161-1169.

"Coding sequence" refers to that portion of a nucleic acid or polynucleotide (e.g., a gene, mRNA, cDNA, etc.) that encodes a peptide or polypeptide.

"Naturally occurring" or "wild-type" refers to the form of a material or substance as found in nature. For example, a naturally occurring or wild-type polypeptide or polynucleotide sequence is a sequence present in an organism that can be isolated from a source in nature and which has not been modified by human manipulation.

"Recombinant" when used with reference to, e.g., a cell, a nucleic acid, or a polypeptide, refers to a material, or a material corresponding to the natural or native form of the material, that has been modified in a manner such that it exists in nature, or is identical to a material that exists in nature, but is produced or derived from synthetic materials and/or by natural materials that have been manipulated in some way. Non-limiting examples include, among others, cells engineered to express nucleic acid sequences that are not found within the native (non-recombinant) forms of the cell, or that express native genes found within the non-recombinant form of the cell at levels that differ from their native expression levels.

"Percentage of sequence identity," "percent identity," and/or "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence in order to effect optimal alignment. The percentage identity is calculated by dividing the number of matched portions in the comparison window by the total number of positions in the comparison window, and multiplying by 100. The number of matched positions in the comparison window is the sum of the number of positions of the comparison polynucleotide or polypeptide in the window that are identical in sequence to the reference polynucleotide or polypeptide and the number of positions of the reference polynucleotide or polypeptide in the comparison window that align with a gap in the comparison polynucleotide or polypeptide. Determination of optimal alignment and percent sequence identity is performed using the BLAST and BLAST 2.0 algorithms (see, e.g., Altschul et al., 1990, J. Mol. Biol. 215:403-410 and Altschul et al., 1997, Nucleic Acids Res. 25(17):3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, 1990, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989, Proc. Nat'l Acad. Sci. USA 89:10915). Numerous other algorithms are available that function similarly to BLAST in providing percentage identity between sequences.

Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l Acad. Sci. USA 85:2444, by computerized implementations of these algorithms (GAP, BESTFIT, FASTA, and TFASTA in the GCG Wisconsin Software Package), or by visual inspection (see generally, *Current Protocols in Molecular Biology*, F. M. Ausubel et al., eds., Current Protocols, a joint venture between Greene Publishing Associates, Inc. and John Wiley & Sons, Inc., 1995 Supplement).

Additionally, determination of sequence alignment and percent sequence identity can employ the BESTFIT or GAP programs in the GCG Wisconsin Software package (Accelrys, Madison Wis.), using default parameters provided.

"Reference sequence" refers to a specified sequence to which another sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity.

The term "reference sequence" is not intended to be limited to wild-type sequences, and can include engineered, variant and/or altered sequences.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least about 80% sequence identity with a reference sequence. In many embodiments, sequences that share "substantial identity" will be at least 85%, 90%, 95%, 96%, 97%, 98%, or even 99% identical to the reference sequence.

The phrase "corresponding to", "reference to" or "relative to" when used in the context of the numbering of a given amino acid sequence or polynucleotide sequence refers to the numbering of the residues of a specified reference sequence when the given amino acid sequence or polynucleotide sequence is compared to the specific reference sequence. In other words, the residue number or residue position of a given polymer is designated with respect to the reference sequence rather than by the actual numerical position of that residue within the given amino acid or polynucleotide sequence. For example, a given amino acid sequence, such as that of a variant LovD polypeptide, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Increased catalytic activity," when used in the context of the variant LovD polypeptide described herein, refers to a LovD polypeptide that exhibits increased conversion of substrate (for example monacolin J or a salt thereof) to product (for example simvastatin or a salt thereof) as compared to a reference LovD polypeptide, as measured in an in vitro or in vivo assay. The origin of the increase in catalytic activity is not critical. Thus, the increase could be due to changes in one or more of $K_m$, $V_{max}$ or $K_{cat}$ or due to decreased substrate inhibition. In some embodiments, for purposes of comparison, catalytic activity can be conveniently expressed in terms of the percentage of substrate converted to product per unit of enzyme in a specified period of time. Enzymes that convert a greater percentage of substrate to product per unit per period of time than a reference enzyme assayed under identical conditions have increased catalytic activity as compared to the referenced enzyme.

Methods and assays for measuring the catalytic activity of enzymes are well-known in the art. Specific examples useful for LovD polypeptides are provided in the Examples section. For comparative assays carried out with crude cell lysates, identical host cells and expression systems should be used. In addition, the number of cells and amount of LovD polypeptide in each preparation should be determined, as is known in the art.

"Thermostable" or "thermal stable" in the context of LovD polypeptides refer to variant LovD polypeptides that retain at least about 50% of their catalytic activity when exposed to a temperature of 30° C. for a period of 3 hrs. as compared to the catalytic activity exhibited by that variant LovD polypeptide at 25° C. under the same reaction conditions.

"Residue" refers to an amino acid when used in the context of polypeptides and a nucleotide when used in the context of polynucleotides.

"Hydrophilic amino acid or residue" refers to an amino acid having a side chain exhibiting a hydrophobicity of less than zero according to the normalized consensus hydrophobicity scale of Eisenberg et al., 1984, J. Mol. Biol. 179:125-142. Genetically encoded hydrophilic amino acids include Thr (T), Ser (S), His (H), Glu (E), Asn (N), Gln (Q), Asp (D), Lys (K) and Arg (R).

"Acidic amino acid or residue" refers to a hydrophilic amino acid having a side chain exhibiting a pKa value of less than about 6 when the amino acid is included in a peptide or polypeptide. Acidic amino acids typically have negatively charged side chains at physiological pH due to loss of a hydrogen ion. Genetically encoded acidic amino acids include Glu (E) and Asp (D).

"Basic amino acid or residue" refers to a hydrophilic amino acid or residue having a side chain exhibiting a pKa value of greater than about 6 when the amino acid is included in a peptide or polypeptide. Basic amino acids typically have positively charged side chains at physiological pH due to association with hydronium ion. Genetically encoded basic amino acids include Arg (R), His (H) and Lys (K).

"Polar amino acid or residue" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q), Ser (S) and Thr (T).

"Hydrophobic amino acid or residue" refers to an amino acid having a side chain exhibiting a hydrophobicity of greater than zero according to the normalized consensus hydrophobicity scale of Eisenberg et al., 1984, J. Mol. Biol. 179:125-142. Genetically encoded hydrophobic amino acids include Pro (P), Ile (I), Phe (F), Val (V), Leu (L), Trp (W), Met (M), Ala (A) and Tyr (Y).

"Aromatic amino acid or residue" refers to a hydrophilic or hydrophobic amino acid having a side chain that includes at least one aromatic or heteroaromatic ring. Genetically encoded aromatic amino acids include Phe (F), Tyr (Y) and Trp (W). Owing to the pKa of its heteroaromatic ring nitrogen, His (H) is classified herein as a hydrophobic or basic residue. It is additionally classified as an aromatic residue due to its heteroaromatic side chain.

"Constrained amino acid or residue" refers to an amino acid that has a constrained geometry. Herein, constrained residues include Pro (P).

"Non-polar amino acid or residue" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded non-polar amino acids include Gly (G), Leu (L), Val (V), Ile (I), Met (M) and Ala (A).

"Aliphatic amino acid or residue" refers to a hydrophobic amino acid or residue having an aliphatic hydrocarbon side chain. Genetically encoded aliphatic amino acids include Ala (A), Val (V), Leu (L) and Ile (I).

Cysteine is unusual in that it can form disulfide bridges with other Cys residues or other sulfanyl- or sulfhydryl-containing amino acids. "Cysteine-like residues" include cysteine and other amino acids that contain sulfhydryl moieties that are available for formation of disulfide bridges. The ability of Cys (and other amino acids with —SH containing side chains) to exist in a polypeptide in either the reduced free —SH or oxidized disulfide-bridged form affects whether it contributes net hydrophobic or hydrophilic character to the polypeptide. While Cys exhibits a hydrophobicity of 0.29 according to the normalized consensus scale of Eisenberg (Eisenberg et al., 1984, supra), it is to be understood that for purposes of the present disclosure, Cys is categorized into its own unique group.

"Small amino acid or residue" refers to an amino acid having a side chain that is composed of a total of three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include Ala (A), Val (V), Cys (C), Asn (N), Ser (S), Thr (T) and Asp (D).

"Hydroxyl-containing amino acid or residue" refers to an amino acid containing a hydroxyl (—OH) moiety. Genetically-encoded hydroxyl-containing amino acids include Ser (S) Thr (T) and Tyr (Y).

"Conservative" amino acid substitutions or mutations refer to those substitutions and mutations in which amino acid residues of a reference polypeptide are replaced with amino acid residues having similar physicochemical properties. Substitutions and mutations that are considered conservative are well-known in the art. In some embodiments, conservative substitutions and mutations are those in which an amino acid of a particular class is replaced with another amino acid within that same class (for example, aliphatic→aliphatic). Exemplary conservative substitutions are provided below:

| Residue | Possible Conservative Mutations |
|---------|--------------------------------|
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R, H) |
| N, Q, S, T | Other polar |
| Y, W, F | Other aromatic (Y, W, F, H) |
| C, P | None |

"Isolated" refers to a substance that has been removed from the source in which it naturally occurs. A substance need not be purified in order to be isolated. For example, a variant LovD polypeptide recombinantly produced in a host cell is considered isolated when it is removed or released from the cell. A variant LovD polypeptide contained within a crude cell lysate fraction is considered "isolated" for purposes of the present disclosure.

"Purified" refers to a substance that has been rendered at least partially free of contaminants and other materials that typically accompany it. Substances can be purified to varying degrees. A substance is "substantially pure" when a preparation or composition of the substance contains less than about 1% contaminants. A substance is "essentially pure" when a preparation or composition of the substance contains less than about 5% contaminants. A substance is "pure" when a preparation or composition of the substance contains less than about 2% contaminants. For substances that are "purified to homogeneity," contaminants cannot be detected with conventional analytical methods.

5.3. LovD VARIANT POLYPEPTIDES

As discussed in the Background Section, the polypeptide encoded by the lovD gene of *A. terreus* is an acyltransferase that catalyzes the last step of lovastatin biosynthesis. This LovD acyltransferase has broad substrate specificity towards the acyl carrier, the acyl substrate and the decalin acceptor (see, e.g., Xie et al., 2006, Chem. Biol. 12:1161-1169) such that the enzyme can be used to transfer acyl groups from thioester co-substrates to decalins such as monacolin J and 6-hydroxy-6-desmethyl monacolin J to yield therapeutically important statin compounds. An exemplary reaction is illustrated in FIG. 1 (boxed region). As illustrated in this FIG. 1 LovD acyltransferase catalytically transfers the α-dimethylbutyryl group of thioester (14) to monacolin J (12) to yield simvastatin (16), making it an attractive target for the preparation of this pharmaceutically important statin.

Despite its attractive catalytic properties, attempts to use isolated *A. terreus* LovD acyltransferase and certain mutants thereof in vitro for production of simvastatin have not been very successful. Stability, solubility, mis-folding, aggregation and reaction rate all proved problematic (see, e.g., Xie & Tang, 2007, Appln. Environ. Microbiol. 73:2054-2060; Xie et al., 2009, Biotech. Bio. Eng. 102:20-28).

The instant disclosure provides variant LovD polypeptides that, like the wild-type LovD acyltransferase from *A. terreus* (SEQ ID NO:2), catalytically transfer an acyl group from a thioester co-substrate to monacolin J (or its analogues or derivatives) to yield simvastatin. These variants include mutations at specified positions and exhibit one or more improved properties as compared to the wild-type LovD and transferase of SEQ ID NO:2.

Skilled artisans will appreciate that lovastatin, monacolin J and simvastatin, as well as their analogues and derivatives can exist in various forms including acid, ester, amide and lactone forms. The acid, ester, amide and lactone forms can also be in the form of salts. The acid (R=—OH), ester (R=—O(alkyl)), amide (R=—N(alkyl)$_2$) and lactone forms of these compounds are illustrated below. Unless stated otherwise, "lovastatin" as used herein includes the acid, ester, amide, lactone and salt forms, "monacolin J" as used herein includes the acid, ester, amide, lactone and salt forms and "simvastatin" as used herein includes the acid, ester, amide, lactone and salt forms. These forms can be used in the methods described herein.

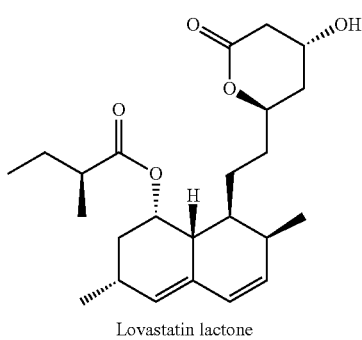

Lovastatin lactone

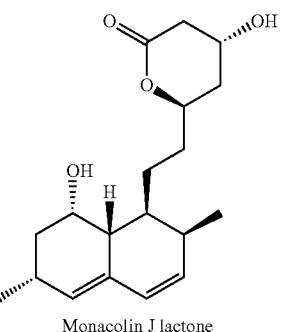

Monacolin J lactone

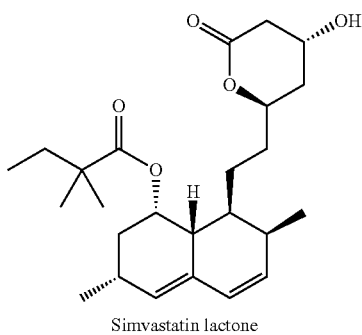

Simvastatin lactone

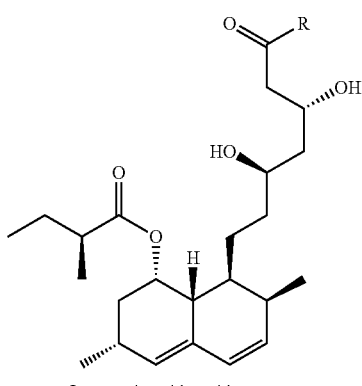

Lovastatin acid, amide or ester

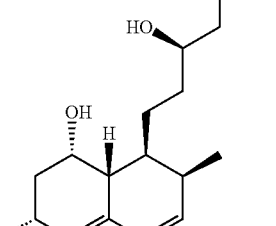

Monacolin J acid, amide or ester

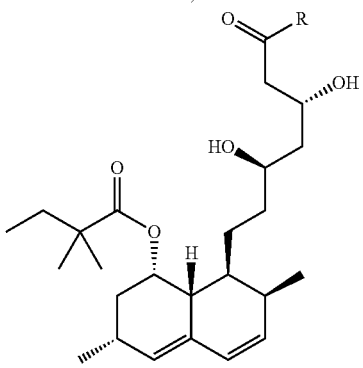

Simvastatin acid, amide, or ester

Mutation experiments carried out with wild-type *A. terreus* LovD acyltransferase revealed that mutations at specified positions correlate with improvements in catalytic activity, thermal stability, stability under conditions of cell lysis and aggregation properties. It was also discovered that a range of mutations could be incorporated at certain positions that, while not providing an identifiable improved property, did not deleteriously affect the overall properties of the polypeptide. All of these various mutations, as well as additional optional conservative mutations, can be used alone and/or in combinations to yield LovD variant polypeptides having specified properties. Significantly, unlike the wild-type *A. terreus* LovD acyltransferase, the variant LovD polypeptides described herein can be isolated and used in in vitro reaction systems to produce therapeutically important statin compounds.

Mutations of the wild-type *A. terreus* LovD acyltransferase of SEQ ID NO:2 that have been found to correlate with increased catalytic activity include, but are not limited to, A123P, M157V, S164V, S172N, L174F, A178L, N191G, L192I, A247S, R250K, S256T, A261H, G275S, Q297G, L361M, V370I and N391S.

Mutations of the wild-type *A. terreus* LovD acyltransferase of SEQ ID NO:2 that have been found to correlate with increased thermal stability include, but are not limited to, Q241M, A261H, Q295R and Q412R.

Mutations of the wild-type *A. terreus* LovD acyltransferase of SEQ ID NO:2 that have been found to correlate with reduced aggregation include, but are not limited to, N43R, D96R and H404K.

Mutations of the wild-type *A. terreus* LovD acyltransferase of SEQ ID NO:2 that have been found to correlate with increased enzyme stability under conditions of cell lysis include, but are not limited to, C40R, C60R and D245E.

Positions within the wild-type *A. terreus* LovD acyltransferase of SEQ ID NO:2 that can be mutated without deleterious effect include, but are not limited to, I4N, A9V, K26E, R28K, R28S, I35L, C40A, C40V, C40F, S41R, N43Y, C60F, C60Y, C60N, C60H, S109C, S142N, A184T, A184V, N191S, A261T, A261E, A261V, L292R, Q297E, L355M, A377V, A383V, N391D and H404R.

One important class of variant LovD polypeptides includes LovD polypeptides that exhibit increased catalytic activity as compared to the wild-type *A. terreus* LovD acyltransferase of SEQ ID NO:2. It has been discovered that including greater numbers of mutations increases the catalytic activity of the LovD polypeptide. As illustrated by the exemplary embodiments of variant LovD polypeptides provided in Table 1, infra, combinations of mutations from those identified above can be selected to obtain variant LovD polypeptides having specified catalytic and other properties. In Table 1, the indicated mutations are relative to SEQ ID NO:2 and the Relative Activity is relative to the activity of the wild-type LovD acyltransferase from *A. terreus*. Conditions used for the activity assay are provided in the Examples section.

TABLE 1

| Variant No. | Mutations | Relative Activity |
|---|---|---|
| 120 | A123P; L174F; A178L; N191S; A247S; L361M; | + |
| 4 | I35L; A123P; L174F; A178L; N191S; A247S; L361M; | + |
| 6 | A123P; L174F; A178L; N191S; A247S; G275S; L361M; | + |
| 8 | A123P; L174F; A178L; N191S; A247S; R250K; L361M; | + |
| 10 | A123P; L174F; A178L; N191S; A247S; Q297E; L361M; | + |
| 12 | R28K; A123P; L174F; A178L; N191S; A247S; L361M; | + |
| 14 | A123P; L174F; A178L; A184T; N191S; A247S; L361M; | + |
| 16 | A123P; L174F; A178L; N191S; A247S; Q297E; L361M; | + |
| 18 | A123P; L174F; A178L; N191S; L192I; A247S; L361M; | + |
| 20 | A123P; L174F; A178L; N191S; A247S; R250K; L361M; | + |
| 22 | A123P; L174F; A178L; N191S; A247S; A261E; L361M; | + |
| 24 | A123P; L174F; A178L; N191S; A247S; L361M; H404R; | + |
| 26 | K26E; A123P; L174F; A178L; N191S; A247S; L361M; | + |
| 28 | A123P; S172N; L174F; A178L; N191S; A247S; G275S; L361M; | ++ |
| 30 | A123P; M157V; S172N; L174F; A178L; N191S; A247S; G275S; L361M; | ++ |
| 32 | A123P; L174F; A178L; N191G; A247S; G275S; L361M; | + |
| 34 | A123P; L174F; A178L; N191S; A247S; G275S; L335M; L361M; | + |
| 36 | A123P; L174F; A178L; N191S; A247S; G275S; L361M; H404K; | + |
| 38 | A123P; L174F; A178L; A184V; N191S; A247S; G275S; L361M; | + |
| 40 | D96R; A123P; L174F; A178L; N191S; A247S; G275S; L361M; | + |
| 42 | A123P; L174F; A178L; N191G; A247S; G275S; L361M; | + |
| 44 | A123P; L174F; A178L; N191S; A247S; G275S; L335M; L361M; | + |
| 46 | A123P; L174F; A178L; N191S; A247S; G275S; L292R; L361M; | + |
| 48 | A123P; L174F; A178L; N191S; L192I; A247S; R250K; G275S; Q297E; L361M; | ++ |
| 50 | A123P; L174F; A178L; N191S; L192I; A247S; R250K; G275S; L361M; | ++ |
| 52 | K26E; C40R; N43Y; A123P; L174F; A178L; N191S; L192I; A247S; G275S; L361M; | ++ |
| 54 | K26E; C40R; A123P; L174F; A178L; N191S; L192I; A247S; G275S; L361M; | ++ |
| 56 | K26E; A123P; L174F; A178L; N191S; A247S; G275S; L361M; | + |
| 58 | A9V; K26E; A123P; M157V; S172N; L174F; A178L; N191S; L192I; A247S; R250K; G275S; Q297E; L361M; A383V; | +++ |
| 60 | K26E; A123P; M157V; S172N; L174F; A178L; N191S; L192I; A247S; R250K; G275S; L361M; | +++ |
| 62 | A123P; M157V; S172N; L174F; A178L; N191G; A247S; G275S; L335M; L361M; | ++ |
| 64 | N43R; D96R; A123P; M157V; S172N; L174F; A178L; N191S; A247S; G275S; L361M; H404K; | ++ |
| 66 | A9V; K26E; A123P; M157V; S172N; L174F; A178L; N191S; L192I; A247S; R250K; S256T; G275S; Q297E; L361M; A383V; | +++ |
| 68 | A9V; K26E; S41R; A123P; M157V; S172N; L174F; A178L; N191S; L192I; A247S; R250K; A261V; G275S; Q297E; L361M; A383V; | +++ |
| 70 | A9V; K26E; R28K; A123P; M157V; S164G; S172N; L174F; A178L; N191G; L192I; Q241M; A247S; R250K; G275S; Q297E; L361M; V370I; A383V; | +++ |
| 72 | A9V; K26E; R28K; C40R; A123P; M157V; S164G; S172N; L174F; A178L; N191G; L192I; Q241M; A247S; R250K; G275S; Q297E; L361M; V370I; A383V; | +++ |
| 74 | A9V; K26E; R28K; C40R; A123P; M157V; S164G; S172N; L174F; A178L; N191G; L192I; Q241M; A247S; R250K; G275S; Q297E; L361M; V370I; A383V; | +++ |
| 76 | A9V; K26E; A123P; M157V; S164G; S172N; L174F; A178L; N191G; L192I; A247S; R250K; G275S; Q297E; L361M; V370I; A377V; A383V; | +++ |
| 78 | A9V; K26E; N43R; A123P; M157V; S164G; S172N; L174F; A178L; N191G; L192I; Q241M; A247S; R250K; G275S; Q297E; L361M; V370I; A383V; H404K; | ++++ |
| 80 | A9V; K26E; N43R; D96R; A123P; M157V; S164G; S172N; L174F; A178L; N191G; L192I; Q241M; A247S; R250K; G275S; Q297E; L361M; V370I; A383V; H404K; | ++++ |
| 82 | A9V; K26E; D96R; A123P; M157V; S164G; S172N; L174F; A178L; N191G; L192I; Q241M; A247S; R250K; G275S; Q297E; L361M; V370I; A383V; | ++++ |
| 84 | A9V; K26E; D96R; A123P; M157V; S172N; L174F; A178L; N191G; L192I; Q241M; A247S; R250K; G275S; Q297E; L361M; V370I; A383V; | +++ |
| 86 | A9V; K26E; N43R; D96R; A123P; M157V; S164G; S172N; L174F; A178L; N191G; L192I; A247S; R250K; G275S; Q297E; L361M; V370I; A383V; H404K; | +++ |

TABLE 1-continued

| Variant No. | Mutations | Relative Activity |
|---|---|---|
| 88 | A9V; K26E; N43R; D96R; A123P; M157V; S164G; S172N; L174F; A178L; N191G; L192I; Q241M; A247S; R250K; G275S; Q297E; L361M; V370I; A383V; | ++++ |
| 90 | A9V; K26E; R28S; N43R; A123P; M157V; S164G; S172N; L174F; A178L; N191G; L192I; Q241M; A247S; R250K; D254E; G275S; Q297E; L361M; V370I; A383V; H404K; | ++++ |
| 92 | A9V; K26E; N43R; A123P; M157V; S164G; S172N; L174F; A178L; N191G; L192I; Q241M; A247S; R250K; A261V; G275S; Q295R; Q297E; L361M; V370I; A383V; H404K; Q412R; | ++++ |
| 94 | A9V; K26E; N43R; A123P; M157V; S164G; S172N; L174F; A178L; N191G; L192I; Q241M; A247S; R250K; A261V; G275S; Q297E; L361M; V370I; A383V; H404K; | ++++ |
| 96 | A9V; K26E; N43R; A123P; M157V; S164G; S172N; L174F; A178L; N191G; L192I; Q241M; A247S; R250K; A261V; G275S; Q295R; Q297E; L361M; V370I; A383V; N391D; H404K; | ++++ |
| 98 | A9V; K26E; N43R; A123P; M157V; S164G; S172N; L174F; A178L; N191G; L192I; Q241M; A247S; R250K; S256T; A261V; G275S; Q297G; L361M; V370I; A383V; N391S; H404K; | ++++ |
| 100 | A9V; K26E; N43R; A123P; M157V; S164G; S172N; L174F; A178L; N191G; L192I; Q241M; A247S; R250K; S256T; A261V; G275S; Q297G; L361M; V370I; A383V; N391S; H404K; | ++++ |
| 102 | A9V; K26E; N43R; S109C; A123P; M157V; S164G; S172N; L174F; A178L; N191G; L192I; Q241M; A247S; R250K; S256T; A261V; G275S; Q297G; L361M; V370I; A383V; N391S; H404K; | ++++ |
| 104 | A9V; K26E; N43R; A123P; M157V; S164G; S172N; L174F; A178L; N191G; L192I; Q241M; A247S; R250K; S256T; A261H; G275S; Q297G; L361M; V370I; A383V; N391S; H404K; | ++++ |
| 106 | A9V; K26E; N43R; A123P; M157V; S164G; S172N; L174F; A178L; N191G; L192I; Q241M; A247S; R250K; S256T; A261H; G275S; Q295R; Q297G; L361M; V370I; A383V; N391S; H404K; Q412R; | ++++ |
| 108 | I4N; A9V; K26E; R28S; N43R; A123P; M157V; S164G; S172N; L174F; A178L; N191G; L192I; Q241M; A247S; R250K; S256T; A261H; G275S; Q297G; L361M; V370I; A383V; N391S; H404K; | ++++ |
| 110 | I4N; A9V; K26E; R28S; N43R; A123P; M157V; S164G; S172N; L174F; A178L; N191G; L192I; Q241M; A247S; R250K; D254E; S256T; A261H; G275S; Q297G; L361M; V370I; A383V; N391S; H404K; | ++++ |
| 112 | I4N; A9V; K26E; R28S; N43R; S109C; A123P; M157V; S164G; S172N; L174F; A178L; N191G; L192I; Q241M; A247S; R250K; S256T; A261H; G275S; Q295R; Q297G; L361M; V370I; A383V; N391S; H404K; Q412R; | ++++ |
| 114 | I4N; A9V; K26E; R28S; I35L; N43R; D96R; A123P; M157V; S164G; S172N; L174F; A178L; N191G; L192I; Q241M; A247S; R250K; S256T; A261H; G275S; Q297G; L335M; L361M; V370I; A383V; N391S; H404K; | ++++ |
| 116 | I4N; A9V; K26E; R28S; I35L; N43R; D96R; S109C; A123P; M157V; S164G; S172N; L174F; A178L; N191G; L192I; Q241M; A247S; R250K; S256T; A261H; G275S; Q297G; L335M; L361M; V370I; A383V; N391S; H404K; | ++++ |
| 118 | I4N; A9V; K26E; R28S; I35L; C40R; N43R; C60R; D96R; S109C; A123P; M157V; S164G; S172N; L174F; A178L; N191G; L192I; Q241M; A247S; R250K; D254E; S256T; A261H; G275S; Q297G; L335M; L361M; V370I; A383V; N391S; H404K; | ++++ |

In Table 1, variants with a relative activity of "+" exhibited from about 10 to 50-fold greater activity than wild-type; variants with a relative activity of "++" exhibited from about 50 to 100-fold greater activity than wild type; variants with a relative activity of "+++" exhibited from about 100 to 500-fold greater activity than wild type; and variants with a relative activity of "++++" exhibited from about 500 to 2000-fold greater activity than wild type.

In some embodiments, mutations are selected from those identified above to yield variant LovD polypeptides exhibiting at least two-fold greater catalytic activity than the wild-type A. terreus LovD. Such variant LovD polypeptides have amino acid sequences that correspond to SEQ ID NO:2, but include at least the following two mutations: L174F and A178L, and optionally from one to about 30 additional mutations selected from the various mutations identified above, and optionally from about one to 20 additional conservative mutations.

In some embodiments, mutations are selected from those identified above to yield variant LovD polypeptides exhibiting at least about 10-fold greater catalytic activity than the wild-type A. terreus LovD. Such variant LovD polypeptides have amino acid sequences that correspond to SEQ ID NO:2, but include at least the following mutations: A123P, L174F, A178F, N191(S or G), A247S and L361M, and from zero to about 26 additional mutations selected from the various mutations identified above, and optionally from about 1 to about 20 additional conservative mutations. Specific exemplary variant LovD polypeptides are provided in Table 1.

In some embodiments, the variant LovD polypeptides have amino acid sequences that correspond to the variant LovD polypeptides of Table 1 and include one or more conservative amino acid substitutions, typically at residue positions that are not mutated as compared to SEQ ID NO:2. In some embodiments, the number of conservative amino acid substitutions is selected such that the sequence of a specific variant LovD polypeptide retains at least about 80%, 81%, 82%, 83%, 84%, 85%, 86%, 87%, 88%, 89%, 90%, 91%, 92%, 93%, 94%, 95%, 96%, 97%, 98% or 99% identity with the specific reference variant LovD polypeptide.

The mutations identified above, along with the specific exemplary variant LovD polypeptides provided in Table 1, can be used to create variant LovD polypeptides having specific properties. For example, variant LovD polypeptides having greater thermal stability than the wild-type *A. terreus* acyltransferase of SEQ ID NO:2 can be obtained by including one of or more mutations identified above that correlate with increased thermal stability. By "mixing and matching" mutations from the different categories, variant LovD polypeptides having improvements in one or more different properties can be readily obtained.

In some embodiments, mutations are selected such that the variant LovD polypeptides are thermally stable.

In some embodiments, mutations are selected such that the variant LovD polypeptides are more stable to conditions of cell lysis than the wild-type *A. terreus* aclytransferase of SEQ ID NO:2. Increased stability to cell lysis can be measured by pre-incubating the lysate at an elevated temperature (for example, 35 to 45° C.) and finding residual activity.

In some embodiments, mutations are selected such that the variant LovD polypeptides exhibit less aggregation than the wild-type *A. terreus* acyltransferase of SEQ ID NO:2 as determined in, for example, 100 mM triethanolamine buffer at a pH of 8 to 9 and at a temperature of 25° C.

Skilled artisans will appreciate that in many instances, the full length variant LovD polypeptide is not necessary for the enzyme to retain catalytic activity. Accordingly, truncated analogs and catalytically active fragments of the variant LovD polypeptides are contemplated. For example, in some embodiments, 1, 2, 3, 4, 5, 6, 7, 8, 9 or 10 amino acids may be omitted. In additional embodiments, variant LovD polypeptides include truncated polypeptides wherein 1 to 15 amino acids may be omitted from the N-terminus and 1 to 6 amino acids may be omitted from the C-terminus. Any specific truncated analog or fragment can be assessed for catalytic activity utilizing the assays provided in the Examples section.

Likewise, additional amino acid residues can be added to one or both termini without deleteriously affecting catalytic activity. Accordingly, while many exemplary embodiments of the variant LovD polypeptides described herein contain 413 amino acid residues, analogs that include from about 1 to about 434 additional amino acids at one or both termini are also contemplated. The additional sequence may be functional or non-functional. For example, the additional sequence may be designed to aid purification, act as a label, or perform some other function. Thus, the variant LovD polypeptides of the disclosure can be in the form of fusion polypeptides in which the variant LovD polypeptides (or fragments thereof) are fused to other polypeptides, such as, by way of example and not limitation, antibody tags (e.g., myc epitope), purifications sequences (e.g., His tags for binding to metals), and cell localization signals (e.g., secretion signals).

The variant LovD polypeptides can be obtained by conventional means, including chemical synthesis and recombinant expression. Polynucleotides and host cells useful for recombinant expression are described below. Variant LovD polypeptides obtained by synthetic means can include non-genetically encoded amino acids, as is known in the art. Commonly encountered non-encoded amino acids that can be included in synthetic variant LovD polypeptides include, but are not limited to: 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutamic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, *CRC Practical Handbook of Biochemistry and Molecular Biology*, CRC Press, Boca Raton, Fla., at pp. 3-70 and the references cited therein, all of which are incorporated by reference). These amino acids may be in either the L- or D-configuration and are preferable in the L-configuration.

When utilized, such non-encoded amino acids are generally selected such that they are conservative substitutions as compared to the reference sequence. Non-encoded amino acids can impart the variant LovD polypeptides with improved properties, such as, for example, increased solubility in desired solvents, increased stability to proteases, etc. Such non-encoded amino acids will typically be included at only a few residue positions, for example, such that greater than 98% or 99% of the variant LovD polypeptide is composed of genetically encoded amino acids.

5.4. NUCLEIC ACIDS

In another aspect, the present disclosure provides polynucleotides encoding the variant LovD polypeptides. The polynucleotides may be operatively linked to one or more regulatory sequences that control gene expression to create a recombinant polynucleotide capable of expressing the variant LovD polypeptide. Expression constructs comprising a polynucleotide sequence encoding a variant LovD polypeptide can be introduced into appropriate host cells to express the corresponding variant LovD polypeptide.

Because of the known genetic code, availability of a polypeptide sequence provides a description of all the polynucleotides capable of encoding that polypeptide. The degeneracy of the genetic code yields an extremely large number of nucleic acids encoding a specific variant LovD polypeptide. Thus, having identified a particular polypeptide sequence, those skilled in the art could make any number of different nucleic acids encoding that polypeptide sequence by simply modifying the sequence of one or more codons in a way that does not alter the encoded sequence. In this regard, the present disclosure specifically contemplates each and every possible individual polynucleotide that encodes a specified polypeptide sequence, and all such individual nucleic acids are to be considered specifically disclosed for any variant LovD polypeptide disclosed herein.

In some embodiments, the polynucleotides comprise codons that are optimized for expression in a specific type of host cell. Codon usage and biases for a variety of different types of microorganisms are well known, as are optimized codons for expression of specific amino acids in each of these microorganisms. (See, e.g., Andersson, S G, and C G Kurland, 1990, Microbiol. Mol. Biol. Rev. 54(2): 198-210. Ermolaeva, M D., 2001, Current Issues in Molecular Biology 3(4): 91-97).

In some embodiments, the polynucleotides encoding the variant LovD polypeptides can be provided as expression vectors, where one or more control sequences are present to regulate the expression of the polynucleotides. Manipulation of the isolated polynucleotide prior to its insertion into a vector may be desirable or necessary depending on the expression vector. Techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2006.

In some embodiments, the control sequences include among others, promoters, leader sequences, polyadenylation sequences, propeptide sequences, signal peptide sequences, and transcription terminators. For bacterial host cells, suitable promoters for directing transcription encoding sequence include, but are not limited to, promoters obtained from the *E. coli* lac operon, *E. coli* trp operon, bacteriophage *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25).

For filamentous fungal host cells, suitable promoters include, but are not limited to, promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (see, e.g., WO 96/00787, which is hereby incorporated by reference herein), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, that is, a sequence recognized by a host cell to terminate transcription. The terminator sequence is operably linked to the 3' terminus of the nucleic acid sequence encoding the polypeptide. Any terminator which is functional in the host cell of choice may be used.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo & Sherman, 1995, Mol. Cell Bio. 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen & Palva, 1993, Microbiol. Rev. 57: 109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (see, e.g., WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to include regulatory sequences that permit regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those that allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the transaminase polypeptide of the present invention would be operably linked with the regulatory sequence.

Thus, in another embodiment, the present disclosure is also directed to a recombinant expression vector comprising a polynucleotide encoding a variant LovD polypeptide, or a catalytically active fragment thereof, and one or more expression regulating regions such as a promoter and a terminator, a replication origin, etc., depending on the type of hosts into which they are to be introduced. The various nucleic acid and control sequences described above may be joined together to produce an expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence positioned within the vector so that the coding sequence is operably linked with the appropriate control sequences for expression.

The expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector may contain one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol, or tetracycline resistance. Suitable markers for yeast host cells are ADE2, HIS3, LEU2, LYS2, METS, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

Expression vectors for expressing the variant LovD polypeptides can contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori (as shown in the plasmid of FIG. 5) or the origins of replication of plasmids pBR322, pUC19, pACYC177 (which plasmid has the P15A ori), or pACYC184 permitting replication in *E. coli*, and pUB110, pE194, pTA1060, or pAM131 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich, 1978, Proc Natl Acad Sci. USA 75:1433).

More than one copy of a variant LovD-encoding nucleic acid may be inserted into a host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the vectors useful for expressing variant LovD polypeptides are commercially available. Suitable commercial expression vectors include p3xFLAGTMTM expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(-) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, Gene 57:193-201).

5.5. METHODS OF MAKING THE LovD VARIANT POLYPEPTIDES AND NUCLEIC ACIDS

Variant LovD polypeptides and polynucleotides encoding such polypeptides can be prepared using methods commonly used by those skilled in the art.

Variants of specifically disclosed variants can be obtained by subjecting the polynucleotide encoding the variant to mutagenesis and/or directed evolution methods. An exemplary directed evolution technique is mutagenesis and/or DNA shuffling as described in Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746 (each of which is hereby incorporated by reference herein).

Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529). Mutagenesis and directed evolution techniques useful for obtaining additional variants are also described in the following references: Ling et al., 1997, "Approaches to DNA mutagenesis: an overview," Anal. Biochem. 254(2):157-78; Dale et al., 1996, "Oligonucleotide-directed random mutagenesis using the phosphorothioate method," Methods Mol. Biol. 57:369-74; Smith, 1985, "In vitro mutagenesis," Ann. Rev. Genet. 19:423-462; Botstein et al., 1985, "Strategies and applications of in vitro mutagenesis," Science 229: 1193-1201; Carter, 1986, "Site-directed mutagenesis," Biochem. J. 237:1-7; Kramer et al., 1984, "Point Mismatch Repair," Cell 38:879-887; Wells et al., 1985, "Cassette mutagenesis: an efficient method for generation of multiple mutations at defined sites," Gene 34:315-323; Minshull et al., 1999, "Protein evolution by molecular breeding," Curr Opin Chem Biol 3:284-290; Christians et al., 1999, "Directed evolution of thymidine kinase for AZT phosphorylation using DNA family shuffling," Nature Biotech 17:259-264; Crameri et al., 1998, "DNA shuffling of a family of genes from diverse species accelerates directed evolution," Nature 391:288-291; Crameri et al., 1997, "Molecular evolution of an arsenate detoxification pathway by DNA shuffling," Nature Biotech 15:436-438; Zhang et al., 1997, "Directed evolution of an effective fructosidase from a galactosidase by DNA shuffling and screening," Proc Natl Acad Sci USA 94:45-4-4509; Crameri et al., 1996, "Improved green fluorescent protein by molecular evolution using DNA shuffling,' Nature Biotech 14:315-319; Stemmer, 1994, "Rapid evolution of a protein in vitro by DNA shuffling," Nature 370:389-391; U.S. Pat. No. 6,117,679 (Stemmer, Sep. 12, 2000); U.S. Pat. No. 6,376,246 (Crameri et al., Apr. 23, 2002); U.S. Pat. No. 6,586,182 (Patten et al., Jul. 1, 2003); U.S. Pat. App. No. 2008/0220990 (Fox, Sep. 11, 2008); and U.S. Pat. App. No. 2009/0312196 (Colbeck et al., Dec. 17, 2009).

Variant LovD polypeptides can be obtained via recombinant expression in host cells, as described above. The expressed variant LovD polypeptide can be recovered from the cells and or the culture medium using any one or more of the well known techniques for protein purification, including, among others, lysozyme treatment, sonication, filtration, salting-out, ultra-centrifugation, and chromatography. Suitable reagents for lysing and the high efficiency extraction of proteins from bacteria, such as *E. coli.*, are commercially available under the trade name CelLytic BTM from Sigma-Aldrich of St. Louis Mo.

Chromatographic techniques for isolation and/or purification of the variant LovD polypeptide include, among others, reverse phase chromatography, high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art. In some embodiments, the engineered transaminases can be expressed as fusion proteins with purification tags, such as His-tags having affinity for metals, or antibody tags for binding to antibodies, e.g., myc epitope tag.

In some embodiments, affinity techniques may be used to isolate and/or purify the variant LovD polypeptides. For affinity chromatography purification, any antibody which specifically binds the variant LovD polypeptide may be used. For the production of antibodies, various host animals, including but not limited to rabbits, mice, rats, etc., may be immunized by injection with an engineered polypeptide. The polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

5.6. HOST CELLS

In another aspect, the present disclosure provides a host cell comprising a polynucleotide encoding a variant LovD polypeptide, the polynucleotide being operatively linked to one or more control sequences for expression of the variant LovD in the host cell. Host cells for use in expressing the variant LovD polypeptides described herein are well known in the art and include but are not limited to, bacterial cells, such as *E. coli, Lactobacillus, Streptomyces* and *Salmonella typhimurium* cells; fungal cells, such as yeast cells (e.g., *Saccharomyces cerevisiae* or *Pichia pastoris* (ATCC Accession No. 201178) or filamentous fungal cells (e.g., *Aspergillus, Trichoderma, Humicola,* or *Chrysosporium*); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the variant LovD polypeptide may be introduced into cells by various methods known in the art. Techniques include, among others, electroporation, biolistic particle bombardment, liposome mediated transfection, calcium chloride transfection, and protoplast fusion. Various methods for introducing polynucleotides into cells will be apparent to the skilled artisan.

The preparation of expression vectors suitable for expressing variant LovD polypeptides in *E. coli* host cells is described in the Examples section. Such expression vectors can be used to express variant LovD polypeptides in a variety of different strains of *E. coli* bacterial host cells. A particularly suitable *E. coli* host cell is BL21 and W3110 bioH-knockout. (See, e.g., Xie, Xinkai, and Yi Tang, 2007, Applied and Environmental Microbiology 73(7): 2054-2060; Xie et al., 2006, *Chemistry & Biology* 13(11): 1161-1169; and Xie et al., Metabolic Engineering 9(4): 379-386).

5.7. USES

The variant LovD polypeptides described herein catalyze transfer of an acyl group from thioester co-substrates to monacolin J and analogues or derivatives thereof to yield therapeutically important statin compounds. A specific embodiment of this reaction, in which monacolin J is converted to simvastatin, is illustrated in the boxed region of FIG. 1. Owing to their catalytic and other properties, the variant LovD polypeptides described herein can be used to make large quantities of therapeutically important statins, such as simvastatin, from monacolin J and/or its C8 ester precursors, in high yields. When monacolin J is used as a starting material, simvastatin can be obtained in a single step. Contrast this with the semi-synthetic methods currently utilized to obtain simvastatin (illustrated in FIG. 1 with dashed arrows).

Accordingly, the present disclosure also provides methods of making simvastatin utilizing the variant LovD polypeptides described herein. According to the methods, and in reference to FIG. 1, monacolin J substrate (or a salt thereof such as a sodium salt or an ammonium salt) (12) is contacted with a variant LovD polypeptide in the presence of an α-dimethylbutyryl thioester co-substrate (14) under conditions in which the variant LovD polypeptide transfers the α-dimethylbutyryl group to the C8 position of monacolin J to yield simvastatin (16).

The identity of the α-dimethylbutyryl thioester co-substrate is not critical. The variant LovD polypeptides accept a wide variety of thioester co-substrates. Suitable α-dimethylbutyryl thioester co-substrates useful for producing simvastatin include, but are not limited to, α-dimethylbutyryl-S—N-acetylcysteamine ("DMB-S-NAC"), α-dimethylbutyryl-S-methylthioglycolate ("DMB-S-MTG"), α-dimethylbutyryl-S-methyl mercaptopropionate "DMB-S-MMP"), α-dimethylbutyryl-S-ethyl mercaptoproprionate ("DMB-S-EMP"), α-dimethylbutyryl-S-methyl mercaptobutyrate ("DMB-S-MMB"), α-dimethylbutyryl-S-merceaptopropionic acid ("DMB-S-MPA"), and optionally substituted S-alkyl or optionally substituted S-aryl/heteroaryl thioesters. Any of these thioester co-substrates, or mixtures of such thioester co-substrates, can be used in the methods described herein.

The α-dimethylbutyryl substrate can be prepared from commercially available starting materials using conventional methods. An exemplary reaction for preparing DMB-S-MMP is illustrated below:

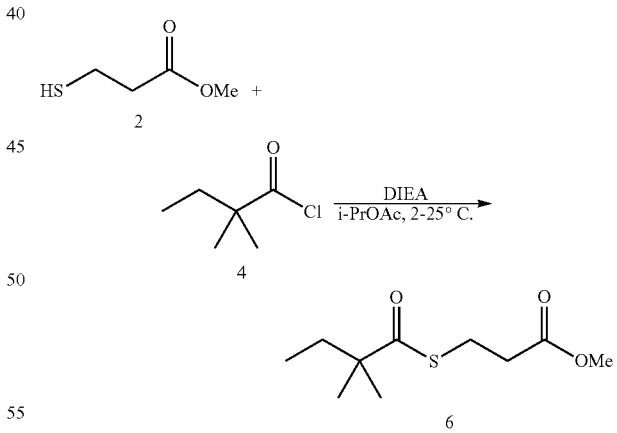

Briefly, methyl 3-merceaptopropionate (2) is acylated with 2,2-dimethylbutanoyl chloride (4) in the presence of N,N-diisopropylamine (DIEA) to yield DMB-S-MMP (6). Specific exemplary reaction conditions are provided in Example 7. Other α-dimethylbutyryl thioester co-substrates can be prepared by routine modification of these methods.

The method can be carried out with a purified variant LovD polypeptide, or, alternatively the LovD polypeptide can be added to the reaction mixture in the form of a crude cell lysate, or a semi-purified cell lysate fraction. Methods for purifying variant LovD polypeptides to a level of purity suitable for use in large scale reactions are provided in Example 3.

The monacolin J substrate (or a salt thereof) can be added to the reaction mixture in purified form, or alternatively, it can be generated in situ by hydrolysis of lovastatin. Methods for obtaining lovastatin and/or monacolin J are well-known. For example, lovastatin can be isolated from *A. terreus* via well-known methods (see, e.g., Endo, A., 1980, The Journal of Antibiotics 33(3): 334-336; Hendrickson et al., 1999, Chemistry & Biology 6(7): 429-439; Kennedy et al., 1999, Science 284(5418): 1368-1372; and Manzoni et al., 2002, Applied Microbiology and Biotechnology 58(5): 555-564). It is also available commercially.

Monacolin J (and salts thereof) can be obtained via alkaline hydrolysis of lovastatin, using conventional methods. A specific exemplary reaction is provided in Example 6.

The reaction can be carried out under a variety of different reaction conditions. Typically the reaction is carried out as a slurry containing about 0.2 to 10 g/L, often 0.25 to 5 g/L, variant LovD polypeptide, from about 1 to 250 g/L, often 50 to 150 g/L, monacolin J substrate (or a salt thereof) and from about 1 to 10 equiv, often 1 to 2 equiv, α-dimethylbutyryl thioester co-substrate. The reaction is typically carried out in an aqueous buffer (0 to 300 mM) having a pH in the range of pH 7.5 to 10.5, often pH 8.5 to 9.5. The identity of the buffer is not critical. Suitable buffers include, but are not limited to, triethanolamine (TEA), potassium phosphate, or a buffer may not be used. Reaction temperatures are from 20 to 50° C., often 20 to 40° C.

Aqueous co-solvent systems can also be used. Such co-solvents will typically include from about 1 to 10% of a polar organic co-solvent. Suitable polar organic co-solvents include, but are not limited to, MeCN, DMSO, isopropyl alcohol (IPA), dioxane, THF, acetone, and MeOH.

It has been discovered that the thiol by product (18 in FIG. 1) generated by the reaction may inhibit the variant LovD polypeptides. Accordingly, it may be desirable to include a thiol scavenging agent in the reaction mixture. Suitable thiol scavenging agents and methods for their use are described in Application No. 61/247,242 titled "Improved Lov-D Acyltransferase Mediated Acylation," filed Sep. 30, 2009, and Application No. PCT/US2010/050253 of the same name filed concurrently herewith under, the disclosures of which are incorporated herein by reference. A preferred thiol scavenging agent is activated charcoal. When used, it can be included in the reaction mixture in an amount ranging from about 2 to 20 g/L. Alternatively, the product may be precipitated as a salt, for example, as an ammonium or sodium salt.

Reaction conditions suitable for use with the variant LovD polypeptides described herein are as follows: 1 to 250 g/L, also 25 to 200 g/L, and often 50 to 150 g/L, monacolin J sodium salt substrate; 1 to 10 equiv, also 1 to 5 equiv, and often 1 to 2 equiv, DMB-S-MMP co-substrate; 0.2 to 10 g/L, often 0.25 to 5 g/L, variant LovD polypeptide (prepared as described in Example 3); 2 to 20 g/L activated charcoal (optional); and 0 to 300 mM TEA buffer, pH 7.5 to 10.5, also pH 8.0 to 10.0, and often pH 8.5 to 9.5.

The reaction is carried out at a temperature in the range of about 20 to 50° C., also 20 to 30° C., and often 20 to 40° C., depending upon the thermostability variant LovD polypeptide used, with agitation or stirring for a duration of about 18 to 48 hours. The progress of the reaction can be monitored by analyzing aliquots via HPLC chromatography as described in the Examples section.

Following the reaction, simvastatin can be isolated from the reaction mixture and converted to pharmaceutically useful salts, such as the ammonium salt, using standard procedures.

Briefly, by-product and excess substrate are extracted with MTBE (2×), the aqueous phases combined and the pH adjusted to pH 5.3-5.4 with 5M HCl while maintaining a temperature of approximately 17° C. EtOAc (13 vol) is added and the mixture agitated for 10 minutes with a flat-blade impeller (345 rpm, 17° C.). The EtOAc washing process is repeated twice more and the three EtOAc extractions combined. The EtOAc extractions are filtered through a Celite pad under reduced pressure, and the filter cake washed with EtOAc. The filtrate and washings are combined and concentrated under reduced pressure to yield simvastatin hydroxy acid.

The hydroxy acid can be converted to the ammonium salt using standard techniques. Specific exemplary conditions are provided in Example 8. Alternatively, the reaction can be run using the ammonium salt of monacolin J, and the simvastatin ammonium salt produced thereby can be isolated directly from the reaction medium by filtration. This process is exemplified in Example 9.

6. EXAMPLES

Example 1

Construction of LovD Genes and Expression Vectors

The acyltransferase encoding gene lovD from wild-type *Aspergillus terreus* (SEQ ID NO:1) was designed for expression in *E. coli* using standard codon optimization (for a recent review of codon optimization software, see Puigbò et al., July 2007, "OPTIMIZER: A Web Server for Optimizing the usage of DNA Sequences," *Nucleic Acids Res.* 2007 35(Web Server issue):W126-31). Genes were synthesized using oligonucleotides composed of 42 nucleotides and cloned into expression vector pCK110900, depicted in FIG. 3 of US Patent Application Publication No. 2006/0195947, which is incorporated herein by reference, under the control of a lac promoter. The expression vector also contained a P15a origin of replication and a chloramphenicol resistance gene. Resulting plasmids were transformed into *E. coli* W3110 or *E. coli* BL21 using standard methods.

Polynucleotides encoding exemplary embodiments of the variant LovD polypeptides of the present disclosure disclosed in Table 1, supra, were also cloned into vector pCK110900 for expression in *E. coli* W3110 or *E. coli* BL21.

Example 2

Shake-Flask Procedure for Production of LovD Polypeptides

A single microbial colony of *E. coli* containing a plasmid encoding a variant LovD polypeptide of interest was inoculated into 50 mL 2×YT broth (1× strength, 16 g/L pancreatic digest of casein (tryptone peptone), 10 g/L yeast extract, 5 g/L sodium chloride) containing 30 μg/ml chloramphenicol and 1% glucose. Cells were grown overnight (at least 16 hours) in an incubator at 30° C. with shaking at 250 rpm. The culture was diluted into 250 ml 2×YT broth containing 30 μg/ml chloramphenicol, in a 1 liter flask to an optical density at 600 nm (OD600) of 0.2 and allowed to grow at 25-30° C. Expression of the lovD gene was induced by addition of isopropyl β D-thiogalactoside ("IPTG") to a final concentration of 1 mM when the OD600 of the culture was 0.6 to 0.8 and incubation was then continued overnight (at least 16 hours).

Cells were harvested by centrifugation (2400 g, 15 min, 4° C.) and the supernatant discarded. The cell pellet was re-suspended with an equal volume of cold (4° C.) 50 mM phosphate buffer (pH 8.5) and harvested by centrifugation as above. The washed cells were re-suspended in two volumes of the cold phosphate buffer and passed through a French Press (18,000 psi, 4° C.). Cell debris was removed by centrifugation (7700 g, 30 min, 4° C.). The clear lysate supernatant was collected and stored at −20° C. Lyophilization of frozen clear lysate provides a dry shake-flask powder of crude LovD polypeptide. Alternatively, the cell pellet (before or after washing) can be stored at 4° C. or −80° C.

Example 3

Fermentation Procedure for Production of LovD Polypeptides

Bench-scale fermentations were begun at 37° C. in an aerated, agitated 15 L fermentor using 6.0 L of growth medium (0.88 g/L ammonium sulfate, 0.98 g/L tri-sodium citrate dihydrate; 12.5 g/L dipotassium hydrogen phosphate trihydrate, 6.25 g/L potassium dihydrogen phosphate, 3.33 g/L Tastone-154 yeast extract, 10 mg/L biotin, 0.083 g/L ferric ammonium citrate, and 8.3 ml/L of a trace element solution containing 2 g/L calcium chloride dihydrate, 2.2 g/L zinc sulfate heptahydrate, 0.5 g/L manganese sulfate monohydrate, 1 g/L cuprous sulfate pentahydrate, 0.1 g/L ammonium molybdate tetrahydrate and 0.02 g/L sodium tetraborate). The fermentor was inoculated with a late exponential culture of *E. coli* W3110 or *E. coli* BL21 containing the plasmid encoding the variant lovD gene of interest (grown in a shake flask as described in Example 2) to a starting OD600 of 0.5 to 2.0. The fermentor was agitated at 500-1500 rpm with air supplied to the fermentation vessel at 2.0-30.0 L/min to maintain a dissolved oxygen level of at least 55%. The pH of the culture was maintained at 7.0 by addition of 28% (v/v) aqueous ammonium hydroxide. Growth of the culture was maintained by addition of a feed solution (up to 4 L) containing 500 g/L glucose, 12 g/L ammonium chloride, 10 mg/L biotin and 5 g/L magnesium sulfate heptahydrate. After addition of 1 L feed volume to the fermentor, at a culture OD600 of approx. 50, expression of the lovD gene was induced by addition of IPTG to a final concentration of 1 mM and fermentation continued at 30° C. for another 18 hrs. The culture was then chilled to 4-8° C. and maintained at that temperature until harvest. Cells were collected by centrifugation (7300 g, 30 min, 4-8° C. Harvested cells were used directly in the recovery process described below or frozen at −20° C. until such use.

The cell pellet was re-suspended and pH adjusted to 8.5 in 2 volumes of 100 mM triethanolamine (chloride) buffer (pH 8.5), at 4° C. to each volume of wet cell paste. The intracellular LovD polypeptide was released from the cells by passing the suspension through a homogenizer fitted with a two-stage homogenizing valve assembly using a pressure of 12000 psi. The cell homogenate was cooled to 4° C. immediately after disruption, the pH was adjusted to 8.5, and then a solution of 11% (w/v) polyethyleneimine, pH 7.2, was added to the lysate to a final concentration of 0.35-0.5% (w/v) and stirred at 600 rpm for 30 minutes at room temperature of 25-30° C. The resulting suspension was clarified by centrifugation (7300 g, 60 min, 4-8° C. The clear supernatant was decanted, its pH adjusted to 8.5, and concentrated eight to ten-fold at 20° C. using a cellulose ultrafiltration membrane (molecular weight cut off 30 KDa). The final concentrate was dispensed into petri plates or into shallow containers, frozen at −20° C. and lyophilized for 48 to 72 hr, with the temperature ramping from −20 to 15° C., to yield a dried powder of crude LovD polypeptide. The crude powder was transferred to polythene bags and stored at −20° C.

Example 4

High-Throughput HPLC Method for Determining Conversion of Monacolin J Sodium Salt to Simvastatin Sodium Salt The degree of conversion of Monacolin J sodium salt to Simvastatin sodium salt was determined using an Agilent HPLC 1200 equipped with a Gemini® C18 column (4.6×50 mm). For the assay, 10 µL samples were eluted with a 52% (v/v) aqueous solution of acetonitrile containing 0.1% trifluoroacetic acid (TFA) at a flow rate of 1.5 mL/min and a temperature of 30° C. The eluate was monitored at 238 nm. Under these conditions, the retention times of Monacolin J acid sodium salt, dimethylbutyryl-S-methylmercaptopropionate (DMB-S-MMP) and Simvastatin sodium salt are approximately 0.8. 2.9, and 3.9 min, respectively. The degree of conversion of Monacolin J sodium salt to Simvastatin sodium salt can be determined using an area-under-the curve analysis.

Example 5

High-Resolution HPLC Method to Determine Conversion of Monacolin J Sodium Salt to Simvastatin Sodium Salt 5 µL of the reaction mixture was taken and dissolved in 1.0 mL of MeCN:water (95:5) mixture. The sample was then centrifuged (300 g, 5 min., 25° C.) to remove precipitated enzyme and the supernatant was analyzed with HPLC. Conversion of Monacolin J sodium salt to Simvastatin hydroxy acid sodium salt were determined using an Agilent HPLC 1200 equipped with a Zorbax Eclipse C18 column (150×4.6 mm, 5 µm) with $H_2O$+0.1% TFA (A) and acetonitrile+0.1% TFA (B) as eluents at a flow rate of 2.0 mL/min at 30° C. and 238 nm. The analysis was run under gradient method with following time and compositions: 0-1 min, 40% B; 1-9 min, 90% B; 9-9.5 min, 90% B; 9.5-10.0 min, 40% B; 10.0-10.5 min, 40% B. Retention times of the Monacolin J hydroxy acid, Monacolin J, dimethylbutyryl-S-methylmercaptopropionate (DMB-S-MMP), Simvastatin hydroxy acid and Simvastatin were approximately 2.0, 3.2, 5.9, 6.4 and 7.7 minutes, respectively.

Example 6

Preparation of Monacolin J from Lovastatin

To lovastatin (30 g, 0.074 mol) in a 3-neck round bottom flask (RBF) fitted with a condenser was added isopropanol (IPA, 250 mL). KOH pellets (33.2 g, 0.593 mol) and water (3 mL, 0.1 vol) were then added to the stirred suspension. The reaction was stirred at 80° C. (internal temperature) for 7 h. The reaction was then cooled to ~50° C. and IPA was removed under reduced pressure (35° C., 50 mbar) until a final volume of ~100 mL (3.3 vol). Water (110 mL, 3.7 vol) was added to the residue and the solution was cooled to ~10° C. in an ice-water bath. 6 M HCl (92 mL, 3.0 vol) was added dropwise to the solution while maintaining the internal temperature between 12-17° C. The pH of the solution was adjusted to a final pH between 3 and 4. The mixture was then stirred in an ice-bath for 2 h. The obtained solid was filtered off and washed with water (60-90 mL, 2-3 vol) and then heptane (60 mL, 2 vol). The filter cake was vacuum dried at 25° C. for 24 h to yield a white solid (22.4 g, 90% yield) with >99% purity by HPLC analysis.

Example 7

Preparation of DMB-S-MMP

A solution of N,N-diisopropylethylamine (19.9 mL, 120 mmol) and methyl 3-mercaptopropanoate (7.21 60 mmol) in isopropyl acetate (i-PrOAc, 100 mL) was cooled to an internal temperature of 2° C. To this vigorously stirred solution, 2,2-dimethylbutanoyl chloride (8.1 g, 60 mmol) was added dropwise over 10 min. The resulting suspension was stirred at 25° C. for 2 h. The reaction was monitored by checking the disappearance of methyl 3-mercaptopropanoate using thin-layer chromatography (TLC) on silica plates. Spots were stained with iodine (eluent: 5% EtOAc/heptane; $R_f$ of methyl 3-mercaptopropanoate: 0.20). The reaction was quenched by addition of saturated ammonium chloride (100 mL) followed by i-PrOAc (100 mL) and the resultant mixture stirred until all solid dissolved. The phases were separated and the organic phase was washed successively with 1% aqueous hydrochloric acid (100 mL) and then water (2×50 mL). The organic phase was then dried over sodium sulfate, filtered, and concentrated under reduced pressure (45° C. bath, 50 mm Hg) to obtain a crude mixture as a pale yellow liquid. The crude mixture is subjected to column chromatography over silica gel using a heptane to 2% EtOAc:heptane gradient. Fractions comprising the pure product were combined and concentrated to afford 10.5 g (80%) of methyl 3-(2,2-dimethylbutanoylthio)propionate (DMB-S-MMP).

Example 8

Conversion of Monacolin J Sodium Salt to Simvastatin Sodium Salt, Purification, Isolation of Simvastatin Hydroxy Acid and Conversion of Simvastatin Hydroxy Acid to Simvastatin Hydroxy Acid Ammonium Salt Variant acyltransferase enzymes, prepared as described in Example 3, were assayed for use in a preparative scale conversion of Monacolin J sodium salt to Simvastatin sodium salt as follows. A 250 mL 3-neck round bottom flask (RBF) was equipped with an overhead stirrer, a flat-blade impeller and an internal thermometer. The reaction vessel was charged with Monacolin J hydroxy acid (5 g, 14.79 mmol). 1M NaOH solution (16.3 mL) and de-ionised water (8.6 mL) were added subsequently. The mixture was stirred until all solid dissolved prior to the addition of the buffer (~5 min). TEA buffer solution (33.3 mL, 400 mM, pH=8.5) was added and the pH of the resultant mixture was adjusted from 9.4 to 9.0 with 5 M HCl (0.15 mL) prior to the addition of enzyme. Variant LovD enzyme (0.05 g) was charged to the stirred mixture as a powder. The mixture was stirred for 5 minutes at 350 rpm at 25° C. to obtain homogeneity. DMB-S-MMP (155 mL, 16.27 mmol, 1.1 eq) was added to start the enzymatic reaction. The resulting biphasic mixture was stirred at 350 rpm at 25° C. (internal temperature). HPLC analysis, as described in Example 5, was performed on samples taken periodically. Approximately 92% conversion was obtained after 72 h. When activated charcoal (10 g/L) was added prior to DMB-S-MMP (to scavenge the by-product, methyl 3-mercaptopropanoate), 95-99% conversion could be obtained after 40-48 hours. In one embodiment, the variant having the mutations described in SEQ ID NO:116 provides good results according to the above conditions. Reaction conditions, including loading amounts of substrate or enzyme, may need to be optimized for the reactivity profile of other variants.

Simvastatin hydroxy acid sodium salt was purified from the above reaction as follows. After in-process analysis indicated maximum conversion, the pH of the reaction mixture was adjusted to 9.0 from 8.2 using 10 M NaOH solution (0.55 mL). If charcoal was added, the reaction mixture was filtered through a pad of Celite (1.5 g) in a standard G4 sintered glass funnel under reduced pressure to remove the charcoal. The 250 mL 3-neck RBF was rinsed with deionised water (5 mL), which was filtered through the same pad of Celite and then combined with the filtrate. The filter cake was washed with water (5 mL) and the washings were collected and combined with the filtrate. MTBE (60 mL; 12 vol) was charged to the reaction and the mixture agitated at 450 rpm for 10 minutes. The 2 phases were then separated and collected separately using a separatory funnel. The aqueous phase was recharged into the 250 mL 3-neck RBF and extracted again with MTBE (30 mL; 6 vol). The phases were separated and collected separately.

Conversion of Simvastatin hydroxy acid sodium salt to Simvastatin hydroxy acid was then performed as follows. EtOAc (65 mL; 13 vol) was charged to the aqueous phase. The pH of the mixture was adjusted to 5.3-5.4 using 5 M HCl solution (0.52 mL) and agitated at 450 rpm for 10 min at 23-25° C. The phases were allowed to separate in a separatory funnel. If an emulsion formed, brine was added to improve separation of two phases. The aqueous layer was removed and the EtOAc phase was collected separately. The aqueous layer was recharged into the 250 ml 3-neck RBF and extracted again with EtOAc (65 mL; 13 vol). The biphasic mixture was agitated at 450 rpm for 10 minutes at 23° C. and then the phases were allowed to separate in a separatory funnel and collected separately. The separatory funnel was rinsed with EtOAc (5 mL), which was then combined with the 1st and 2nd EtOAc extracts. The combined EtOAc extracts were filtered through a pad of Celite (1 g) in a standard G4 sintered glass funnel under reduced pressure to clarify the extract. The filter cake was washed with EtOAc (10 mL) and the washings were combined with the filtrate. The filtrate was concentrated from 145 mL to 65 mL under reduced pressure.

Conversion of Simvastatin hydroxy acid to Simvastatin hydroxy acid ammonium salt was performed as follows. The ethyl acetate solution containing the simvastatin hydroxy acid was charged to a 250 mL 3-neck RBF and the reaction mixture was stirred at 250 rpm at 20-22° C. A 1:1 (v/v) mixture of ammonium hydroxide (2.5 mL) and MeOH (2.5 mL) was then added dropwise over 10 mins to the reaction mixture, maintaining the internal temperature at 20-22° C. After complete addition of the ammonium hydroxide and MeOH mixture, the resultant mixture was stirred at 260 rpm for 1 h at 20-22° C. The slurry was agitated further for 1 h at 0-5° C. The white solid was then filtered through a standard G4 sintered glass funnel under vacuum and the reaction vessel was rinsed with 6.5 mL of cold EtOAc. The rinse was filtered through the same pad of Celite and combined with the filtrate. The filter cake was then washed with cold EtOAc (6.5 mL; 1.3 vol). The white solid was dried in the vacuum oven (2 mm Hg) at 25° C. for 24 h to afford approximately 4.3-5.0 g (65-75% isolated yield) of simvastatin hydroxy acid, ammonium salt as a white solid with chemical purity 94-97% (AUC, 238 nm).

Example 9

Conversion of Monacolin J Hydroxy Acid Ammonium Salt to Simvastatin Hydroxy Acid Ammonium Salt and Isolation of Simvastatin Hydroxy Acid Ammonium Salt Variant acyltransferase enzymes, prepared as described in Example 3, were assayed for use in a preparative scale conversion of Monacolin J ammonium salt to Simvastatin ammonium salt as follows. A 250 mL 3-neck round bottom flask (RBF) was equipped with an overhead stirrer, a flat-blade impeller and an internal thermometer. The reaction vessel was charged with Monacolin J hydroxy acid (10 g, 29.58 mmol). Deionized water (112.0 mL) and $NH_4OH$ (4.2 mL) were added subsequently. The mixture was stirred until all solid dissolved prior to the pH adjustment (~2 min). The pH of the resultant mixture was adjusted from 9.2 to 9.0 with 5 M HCl (1.5 mL) prior to the addition of enzyme. Variant LovD enzyme (0.10 g) was charged to the stirred mixture as a powder. The mixture was stirred for 5 minutes at 300 rpm at 25° C. to obtain homogeneity. DMB-S-MMP (7.1 mL, 32.54 mmol, 1.1 eq) was added to start the enzymatic reaction. The resulting biphasic mixture was stirred at 300 rpm at 25° C. (internal temperature). The pH of the reaction was controlled at 9.0 by pH stat and titration of 25% $NH_4OH$. HPLC analysis, as described in Example 5, was performed on samples taken periodically. Approximately 97% conversion was obtained after 48 h. In one embodiment, the variant having the mutations described in SEQ ID NO:116 provides good results according to the above conditions. Reaction conditions, including loading amounts of substrate or enzyme, may need to be optimized for the reactivity profile of other variants.

Simvastatin hydroxy acid ammonium salt was isolated from the above reaction as follows. After in-process analysis indicated maximum conversion, the reaction mixture was filtered through a standard G4 sintered glass funnel under reduced pressure. The 250 mL 3-neck RBF was rinsed with chilled deionized water (10 mL) and the slurry was filtered through the same sintered glass funnel. The filter cake was washed twice with chilled deionized water (20 mL) and then washed three times with MTBE (40 mL). The white solid was dried in a vacuum oven (2 mmHg) at 25° C. for 24 h to afford approximately 11.4 to 11.7 g (85 to 87% isolated yield) of Simvastatin hydroxy acid ammonium salt as a white solid with a chemical purity of about 97 to 98% (AUC, 238 nm).

All publications, patents, patent applications and other documents cited in this application are hereby incorporated by reference in their entireties for all purposes to the same extent as if each individual publication, patent, patent application or other document was individually indicated to be incorporated by reference for all purposes.

While various specific embodiments have been illustrated and described, it will be appreciated that various changes can be made without departing from the spirit and scope of the invention(s).

What is claimed is:

1. An isolated or recombinant variant LovD polypeptide having at least two-fold greater acyltransferase activity than the wild-type *Aspergillus terreus* acyltransferase of SEQ ID NO:2, which comprises the amino acid sequence of SEQ ID NO:2 that includes the mutations L174F and A178L and from 1 to 30 additional mutations.

2. The variant LovD polypeptide of claim 1, which has at least 10-fold greater acyltransferase activity than the wild-type *A. terrus* acyltransferase of SEQ ID NO:2.

3. The variant LovD polypeptide of claim 1, that includes the following additional mutations: A123P, N191S/G, A247S and L361M.

4. The variant LovD polypeptide of claim 1, wherein the 1 to 30 additional mutations are selected from the group consisting of 14N, A9V, K26E, R28K, R28S, I35L, C40A, C40V, C40F, C40R, S41R, N43R, N43Y, C60F, C60R, C60Y, C60N, C60H, D96R, S109C, A123P, S142N, A184T, A184V, N191S/G, Q241M, A247S, D254E, A261H, A261T, A261E, A261V, L292R, Q295R, Q297E, L335M, L361M, A377V, A383V, N391D, H404K, H404R, Q412R.

5. The variant LovD polypeptide of claim 3, further comprising one or more additional mutations selected from: A9V, K26E, M157V, L192I, R250K, G275S, Q297E/G, and A383V.

6. The variant LovD polypeptide of claim 5, wherein the one or more additional mutations are selected from: A9, K26E, and G275S.

7. A method of making simvastatin comprising contacting monacolin J substrate with a variant LovD polypeptide according to claim 1 in the presence of an α-dimethylbutyryl thioester co-substrate and under conditions in which the monacolin J is converted to simvastatin.

8. The method of claim 7, wherein the monacolin J is a sodium salt.

9. The method of claim 8, wherein the monacolin J is a sodium salt and activated charcoal is added.

10. The method of claim 9, wherein the monacolin J is an ammonium salt.

11. The method of claim 7, wherein an agent for precipitating simvastatin is added.

12. The method of claim 11, wherein said agent is ammonium hydroxide.

13. A method of making simvastatin comprising contacting a lovastatin substrate with a variant LovD polypeptide according to claim 1 in the presence of an α-dimethylbutyryl thioester co-substrate and under conditions in which the lovastatin substrate is converted to simvastatin.

14. The method of claim 13, wherein said lovastatin substrate, said variant LovD polypeptide and said thioester are charges at substantially the same time into a vessel.

15. The method of claim 13, wherein said lovastatin substrate and said variant LovD polypeptide are first charged into a vessel and then said thioester is charged into said vessel.

16. The method of claim 13, wherein an agent for precipitating simvastatin is added.

17. The method of claim 16, wherein said agent is ammonium hydroxide.

* * * * *

```
                        SEQUENCE LISTING

<160> NUMBER OF SEQ ID NOS: 2

<210> SEQ ID NO 1
<211> LENGTH: 1242
<212> TYPE: DNA
<213> ORGANISM: Artificial Sequence
<220> FEATURE:
<223> OTHER INFORMATION: Codon optimized Aspergillus terreus lovD

<400> SEQUENCE: 1
atgggttcta tcattgatgc ggctgcggcc gcggacccgg tggttctgat ggaaacggct      60
ttccgtaaag cggttaaaag ccgccagatt ccgggtgctg ttattatggc gcgtgattgt     120
agtggtaacc tgaactacac tcgctgtttc ggcgcacgca ctgtgcgtcg cgacgagtgc     180
aatcaattac caccgctgca ggtggataca ccatgtcgtc tggcaagcgc tactaaatta     240
ctgaccacga ttatggcact gcagtgcatg gaacgcggcc tggtagactt ggatgaaact     300
gttgaccgcc tgctgccgga cctgagcgcg atgccggtgc tggaaggctt tgatgatgcc     360
ggcaacgccc gtctgcgcga acgccgtggt aaaattacgt tacgccatct gctgacacac     420
accagcggtc tgtcgtacgt cttcctgcat ccgctgctgc gcgagtatat ggcccagggt     480
catttgcaga gcgctgagaa gtttggcatt cagtctcgtc tggcgccgcc agctgttaat     540
gatccaggcg cggaatggat ttatgcgct aatctggact gggcaggcaa attagtggaa     600
cgcgcaacgg gcttggacct ggaacagtac ttgcaggaga acatttgcgc gccgctgggc     660
atcactgata tgacgttcaa actgcagcag cgtccggata tgctggcacg tcgtgccgac     720
cagacccacc gcaactccgc ggatggtcgt ctgcgctatg atgactctgt gtattttcgc     780
gcggacggtg aagagtgttt cggggcag ggcgtgttca gcggtccagg cagttacatg     840
aaggttctgc actctctgct gaaacgtgac ggcctgttgc tgcagccaca aaccgtggat     900
```

```
ctgatgttcc agccggcgct ggaaccgcgc ttggaagaac aaatgaacca gcatatggac    960
gcgtcgccgc acatcaacta tggcggtcca atgcctatgg tcctgcgtcg cagcttcggc   1020
ctgggtggta tcattgcact ggaggatctg gatggtgaga actggcgtcg taaaggctcg   1080
ctgacgtttg gtggcggtcc aaacattgtt tggcagattg acccgaaagc gggtctgtgt   1140 acttttagcct ttttccagct ggaaccgtgg aacgacccgg tgtgtcgtga cctgactcgc   1200
acctttgagc acgcgatcta tgcacagtat caacagggct aa                      1242
```

<210> SEQ ID NO 2
<211> LENGTH: 413
<212> TYPE: PRT
<213> ORGANISM: Artificial Sequence
<220> FEATURE:
<223> OTHER INFORMATION: Codon optimized Aspergillus terreus lovD

<400> SEQUENCE: 2

```
Met Gly Ser Ile Ile Asp Ala Ala Ala Ala Asp Pro Val Val Leu
1               5                   10                  15

Met Glu Thr Ala Phe Arg Lys Ala Val Lys Ser Arg Gln Ile Pro Gly
            20                  25                  30

Ala Val Ile Met Ala Arg Asp Cys Ser Gly Asn Leu Asn Tyr Thr Arg
        35                  40                  45

Cys Phe Gly Ala Arg Thr Val Arg Arg Asp Glu Cys Asn Gln Leu Pro
    50                  55                  60

Pro Leu Gln Val Asp Thr Pro Cys Arg Leu Ala Ser Ala Thr Lys Leu
65                  70                  75                  80

Leu Thr Thr Ile Met Ala Leu Gln Cys Met Glu Arg Gly Leu Val Asp
                85                  90                  95

Leu Asp Glu Thr Val Asp Arg Leu Leu Pro Asp Leu Ser Ala Met Pro
            100                 105                 110

Val Leu Glu Gly Phe Asp Asp Ala Gly Asn Ala Arg Leu Arg Glu Arg
        115                 120                 125

Arg Gly Lys Ile Thr Leu Arg His Leu Leu Thr His Thr Ser Gly Leu
    130                 135                 140

Ser Tyr Val Phe Leu His Pro Leu Leu Arg Glu Tyr Met Ala Gln Gly
145                 150                 155                 160

His Leu Gln Ser Ala Glu Lys Phe Gly Ile Gln Ser Arg Leu Ala Pro
                165                 170                 175

Pro Ala Val Asn Asp Pro Gly Ala Glu Trp Ile Tyr Gly Ala Asn Leu
            180                 185                 190

Asp Trp Ala Gly Lys Leu Val Glu Arg Ala Thr Gly Leu Asp Leu Glu
        195                 200                 205

Gln Tyr Leu Gln Glu Asn Ile Cys Ala Pro Leu Gly Ile Thr Asp Met
    210                 215                 220

Thr Phe Lys Leu Gln Gln Arg Pro Asp Met Leu Ala Arg Arg Ala Asp
225                 230                 235                 240

Gln Thr His Arg Asn Ser Ala Asp Gly Arg Leu Arg Tyr Asp Asp Ser
                245                 250                 255

Val Tyr Phe Arg Ala Asp Gly Glu Glu Cys Phe Gly Gly Gln Gly Val
            260                 265                 270

Phe Ser Gly Pro Gly Ser Tyr Met Lys Val Leu His Ser Leu Leu Lys
        275                 280                 285

Arg Asp Gly Leu Leu Leu Gln Pro Gln Thr Val Asp Leu Met Phe Gln
    290                 295                 300

Pro Ala Leu Glu Pro Arg Leu Glu Glu Gln Met Asn Gln His Met Asp
```

```
                    305                 310                 315                 320

Ala Ser Pro His Ile Asn Tyr Gly Gly Pro Met Pro Met Val Leu Arg
            325                 330                 335

Arg Ser Phe Gly Leu Gly Gly Ile Ile Ala Leu Glu Asp Leu Asp Gly
            340                 345                 350

Glu Asn Trp Arg Arg Lys Gly Ser Leu Thr Phe Gly Gly Gly Pro Asn
            355                 360                 365

Ile Val Trp Gln Ile Asp Pro Lys Ala Gly Leu Cys Thr Leu Ala Phe
        370                 375                 380

Phe Gln Leu Glu Pro Trp Asn Asp Pro Val Cys Arg Asp Leu Thr Arg
385                 390                 395                 400

Thr Phe Glu His Ala Ile Tyr Ala Gln Tyr Gln Gln Gly
                405                 410
```